US010166038B2

(12) United States Patent
Ravikumar et al.

(10) Patent No.: US 10,166,038 B2
(45) Date of Patent: *Jan. 1, 2019

(54) MINIMALLY INVASIVE SURGICAL ASSEMBLY AND METHODS

(71) Applicant: TELEFLEX MEDICAL INCORPORATED, Morrisville, NC (US)

(72) Inventors: Sundaram Ravikumar, Briarcliff Manor, NY (US); H. Allan Alward, Shelton, CT (US); Steven J. Wysocki, Stratford, CT (US); Guy L. Osborne, Trumbull, CT (US); Robert F. Smith, Waterbury, CT (US)

(73) Assignee: Teleflex Medical Incorporated, Morrisville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/345,716

(22) Filed: Nov. 8, 2016

(65) Prior Publication Data

US 2017/0049465 A1    Feb. 23, 2017

Related U.S. Application Data

(63) Continuation of application No. 11/685,522, filed on Mar. 13, 2007, now Pat. No. 9,492,187, which is a (Continued)

(51) Int. Cl.
*A61B 17/28* (2006.01)
*A61B 17/34* (2006.01)
(Continued)

(52) U.S. Cl.
CPC ........ *A61B 17/29* (2013.01); *A61B 17/00234* (2013.01); *A61B 17/221* (2013.01);
(Continued)

(58) Field of Classification Search
CPC ....... A61B 17/28; A61B 17/29; A61B 17/232; A61B 17/32056; A61B 17/2212; A61B 17/50

See application file for complete search history.

(56) References Cited

U.S. PATENT DOCUMENTS 3,817,251 A    6/1974 Hasson
3,844,291 A   10/1974 Moen
(Continued)

*Primary Examiner* — Anh Dang
(74) *Attorney, Agent, or Firm* — Baker Hostetler LLP

(57) ABSTRACT

A minimally invasive surgical assembly broadly includes an outer hollow needle which has an outer diameter of 3.0 mm or smaller, and a coaxial surgical instrument having a shaft which extends through the outer hollow needle. The coaxial surgical instrument includes end effectors at the end of the shaft which are biased to an open position such that when the end effectors of the surgical instrument extended out of the needle they open, and they are closed by relative movement of the needle over them. The assembly preferably includes a first fixing element which is used to fix the relative location of the surgical instrument and the needle. The assembly also preferably includes a second fixing element which moves relative to the needle and is located on the outside thereof and which is used to fix the relative location of the needle to the patient.

18 Claims, 19 Drawing Sheets

Related U.S. Application Data continuation-in-part of application No. 11/420,927, filed on May 30, 2006, now Pat. No. 7,766,937.

(60) Provisional application No. 60/828,916, filed on Oct. 10, 2006, provisional application No. 60/781,556, filed on Mar. 13, 2006.

(51) Int. Cl.

| | | |
|---|---|---|
| *A61B 17/29* | (2006.01) | |
| *A61B 17/221* | (2006.01) | |
| *A61B 90/50* | (2016.01) | |
| *A61B 90/57* | (2016.01) | |
| *A61B 17/068* | (2006.01) | |
| *A61B 17/122* | (2006.01) | |
| *A61B 17/00* | (2006.01) | |
| *A61F 2/00* | (2006.01) | |

(52) U.S. Cl.
CPC ...... *A61B 17/3403* (2013.01); *A61B 17/3417* (2013.01); *A61B 90/50* (2016.02); *A61B 90/57* (2016.02); *A61B 17/068* (2013.01); *A61B 17/122* (2013.01); *A61B 2017/00349* (2013.01); *A61B 2017/00353* (2013.01); *A61B 2017/2215* (2013.01); *A61B 2017/347* (2013.01); *A61B 2017/3407* (2013.01); *A61B 2017/3492* (2013.01); *A61B 2090/571* (2016.02); *A61F 2/0063* (2013.01)

(56) References Cited

U.S. PATENT DOCUMENTS

| | | | |
|---|---|---|---|
| 4,077,412 A | 3/1978 | Moossun | |
| 4,570,642 A | 2/1986 | Kane et al. | |
| 4,723,547 A | 2/1988 | Kullas et al. | |
| 4,923,461 A | 5/1990 | Caspari et al. | |
| 5,073,169 A | 12/1991 | Raiken | |
| 5,147,316 A | 9/1992 | Castillenti | |
| 5,176,643 A | 1/1993 | Kramer et al. | |
| 5,176,697 A | 1/1993 | Hasson et al. | |
| 5,201,742 A | 4/1993 | Hasson | |
| 5,222,973 A | 6/1993 | Sharpe et al. | |
| 5,224,954 A | 7/1993 | Watts et al. | |
| 5,258,005 A * | 11/1993 | Christian | A61B 17/29 606/205 |
| 5,281,237 A | 1/1994 | Gimpelson | |
| 5,290,276 A | 3/1994 | Sewell, Jr. | |
| 5,330,497 A | 7/1994 | Freitas et al. | |
| 5,354,283 A | 10/1994 | Bark et al. | |
| 5,375,588 A | 12/1994 | Yoon | |
| 5,556,411 A | 9/1996 | Taoda et al. | |
| 5,573,530 A | 11/1996 | Fleury et al. | |
| 5,601,571 A | 2/1997 | Moss | |
| 5,626,597 A | 5/1997 | Urban et al. | |
| 5,634,918 A | 6/1997 | Richards | |
| 5,653,716 A | 8/1997 | Malo et al. | |
| 5,658,298 A | 8/1997 | Vincent et al. | |
| 5,814,043 A | 9/1998 | Shapeton | |
| 5,857,999 A | 1/1999 | Quick et al. | |
| 5,893,873 A | 4/1999 | Rader et al. | |
| 5,951,488 A | 9/1999 | Slater et al. | |
| 5,964,740 A | 10/1999 | Ouchi | |
| 5,971,940 A | 10/1999 | Baker et al. | |
| 6,099,550 A | 8/2000 | Yoon | |
| 6,391,046 B1 | 5/2002 | Overaker et al. | |
| 6,616,683 B1 | 9/2003 | Toth et al. | |
| 6,630,103 B2 | 10/2003 | Martin et al. | |
| 6,860,894 B1 | 3/2005 | Pittman | |
| 6,908,454 B2 | 6/2005 | McFarlane | |
| 6,945,984 B2 | 9/2005 | Arumi et al. | |
| 2001/0056286 A1 | 12/2001 | Etter et al. | |
| 2002/0042604 A1 | 4/2002 | Palmer et al. | |
| 2003/0040773 A1 | 2/2003 | Arumi et al. | |
| 2004/0167472 A1 | 8/2004 | Howell et al. | |
| 2004/0230221 A1 | 11/2004 | Gadberry et al. | |
| 2005/0113737 A1 | 5/2005 | Ashby et al. | |
| 2005/0273133 A1 | 12/2005 | Shluzas et al. | |
| 2005/0283163 A1 | 12/2005 | Portney et al. | |

* cited by examiner

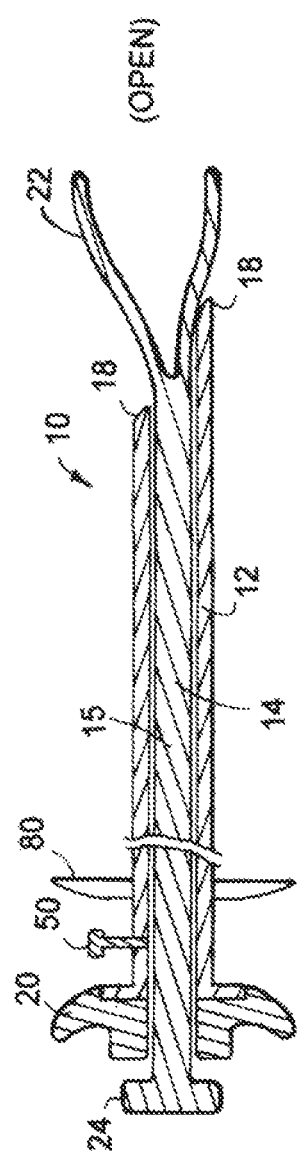
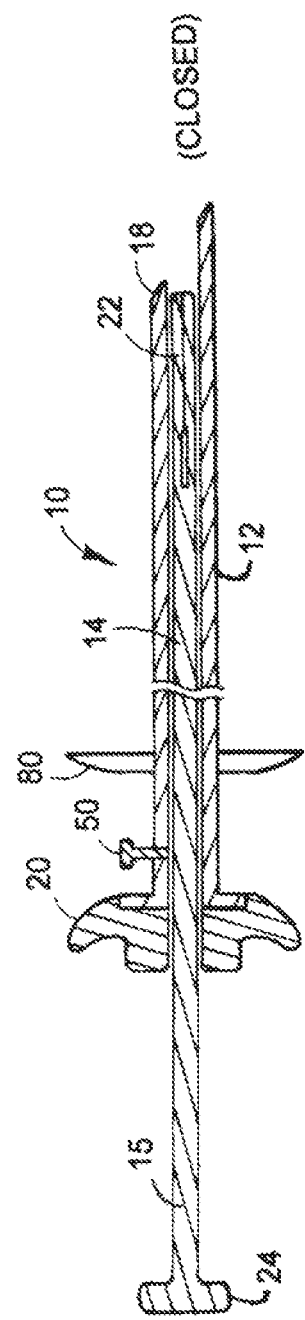

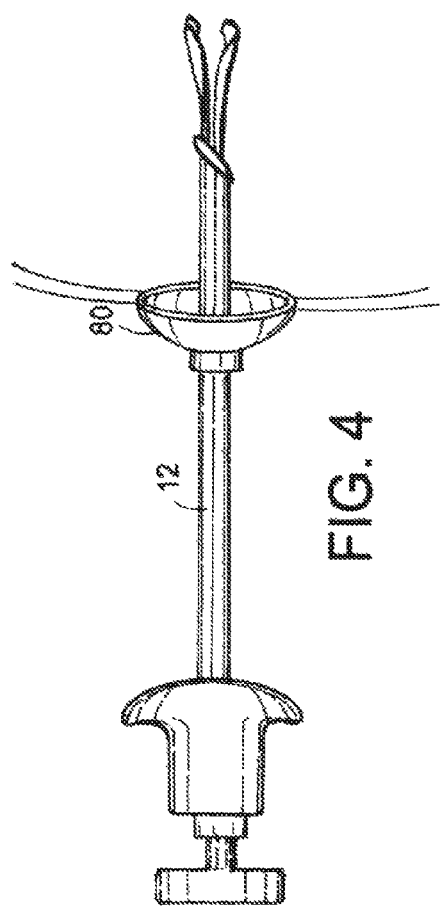
FIG. 4
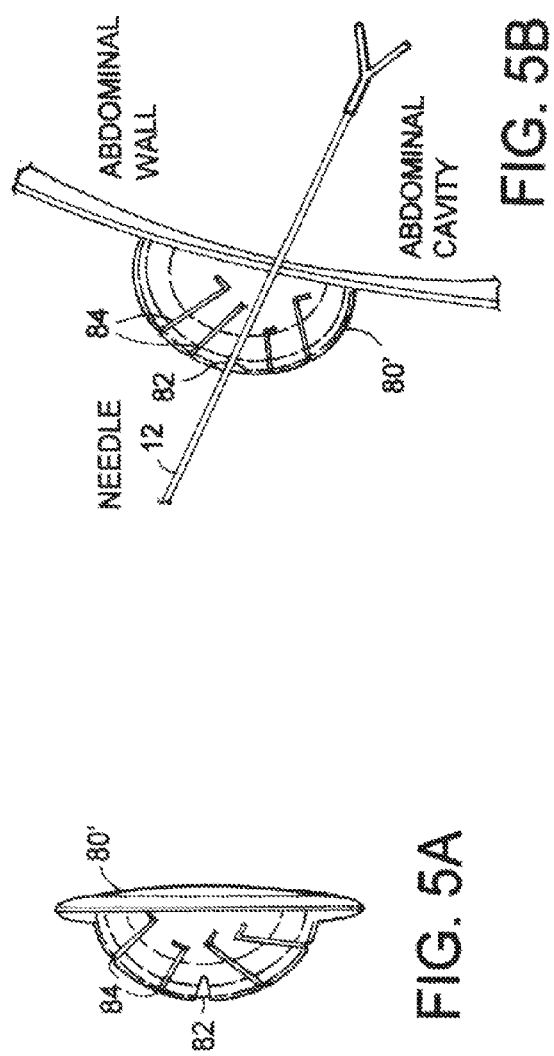
FIG. 5A
FIG. 5B

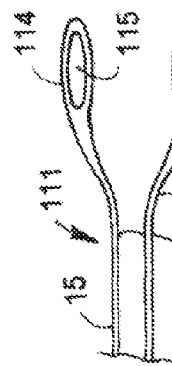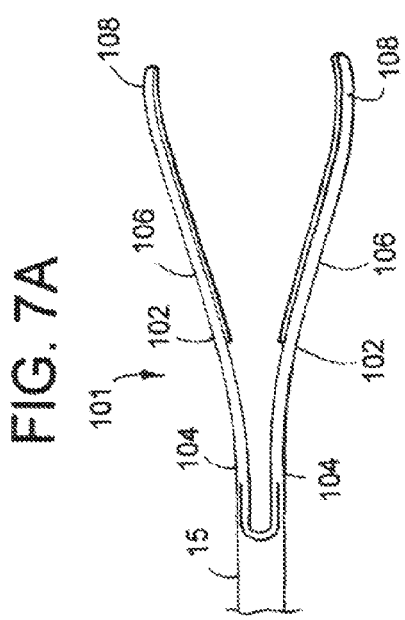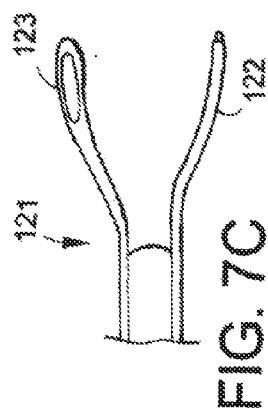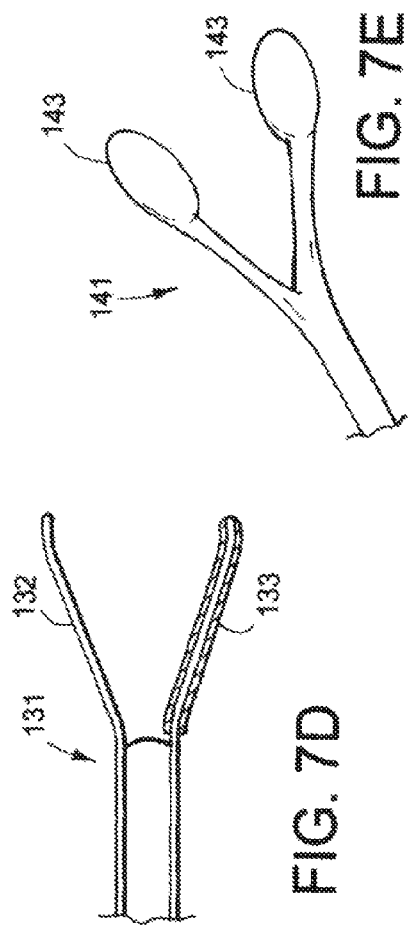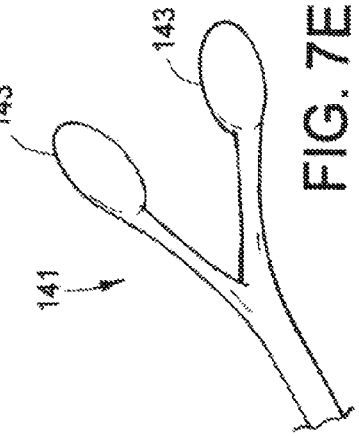

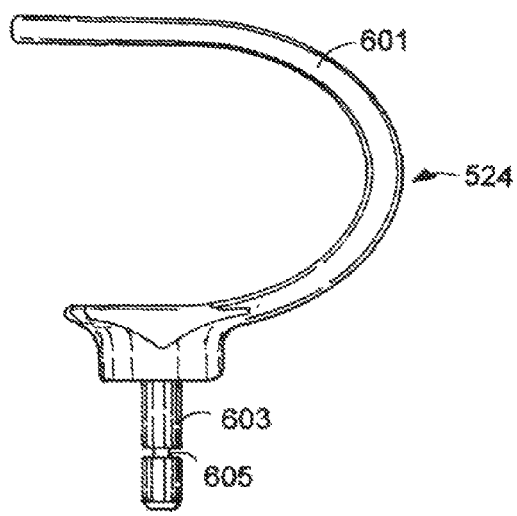
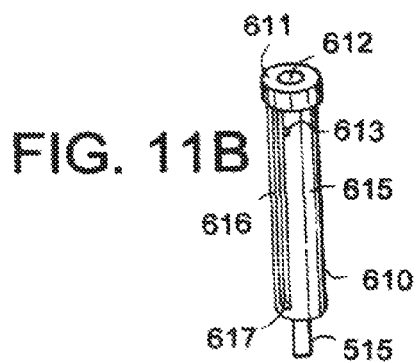
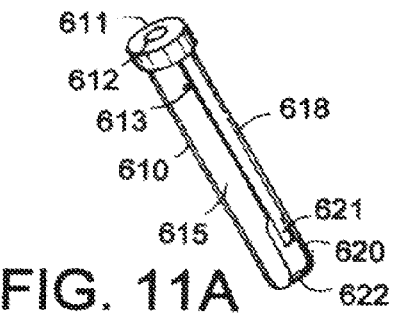
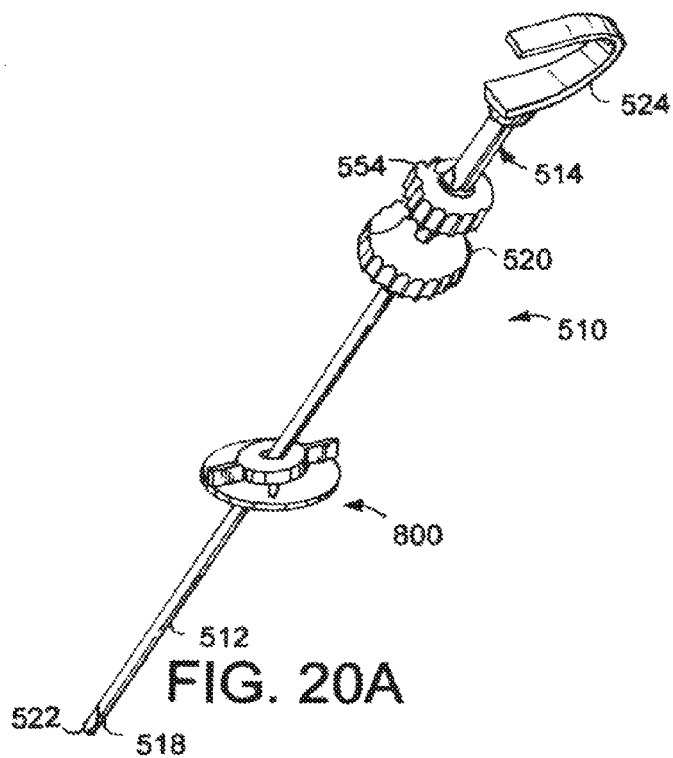
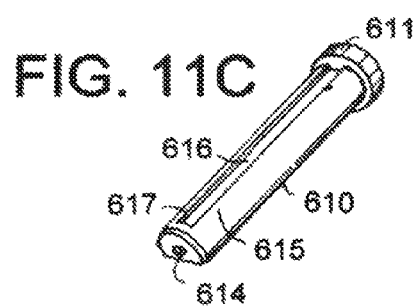

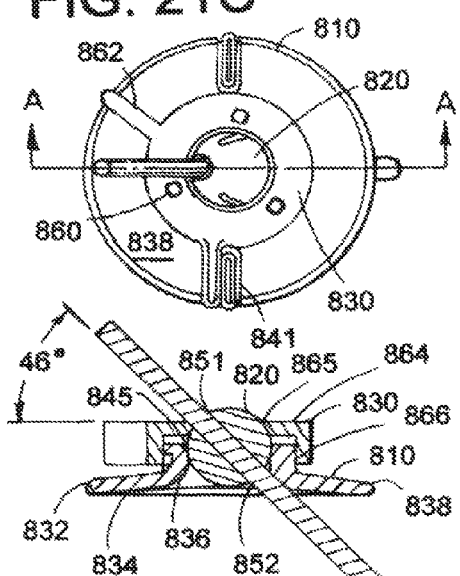
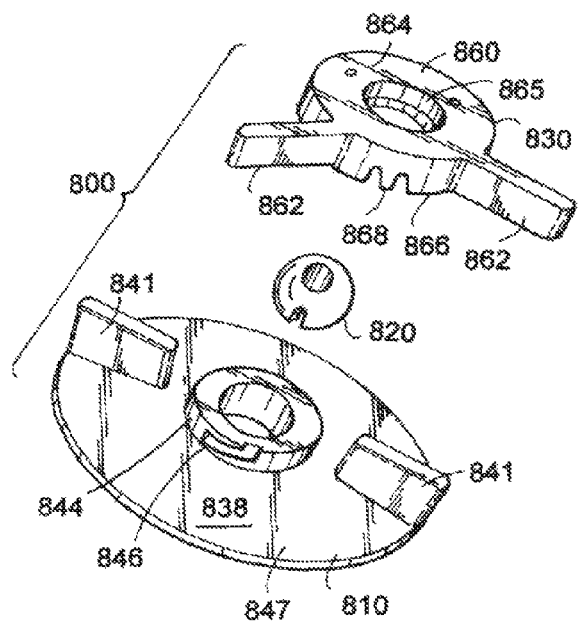
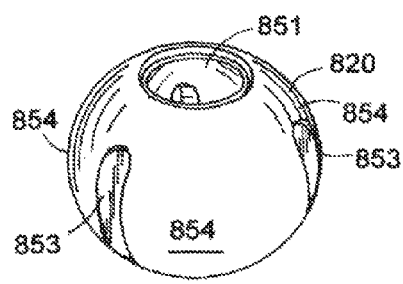
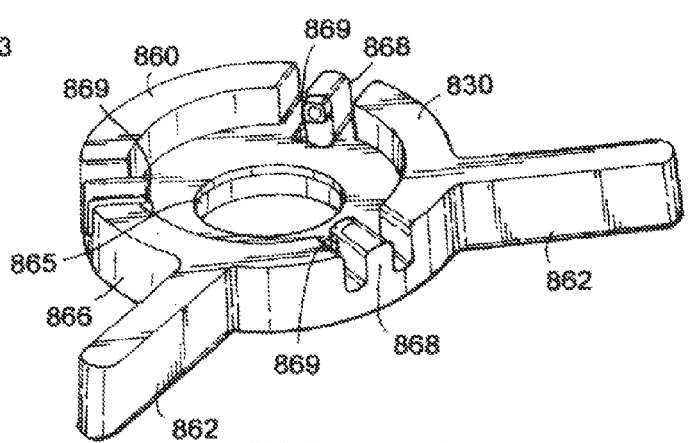

MINIMALLY INVASIVE SURGICAL ASSEMBLY AND METHODS

CROSS-REFERENCE TO RELATED APPLICATION

This patent application is a continuation application and claims the priority benefit of co-pending U.S. patent application Ser. No. 11/685,522 filed Mar. 13, 2007, which claims priority to U.S. Provisional Patent Application No. 60/781,556 filed Mar. 13, 2006, to U.S. Provisional Patent Application No. 60/828,916 filed Oct. 10, 2006, and to U.S. patent application Ser. No. 11/420,927 filed May 30, 2006, all of which are hereby incorporated by reference herein in their entireties by this reference.

BACKGROUND OF THE INVENTION

1. Field of the Invention

This invention relates broadly to surgical instruments and methods of their use. More particularly, this invention relates minimally invasive surgical instruments incorporating a needle and a working device which extends through and beyond the needle and which can be retracted into the needle. The invention has particular application to laparoscopic-type surgery, although it is not limited thereto.

2. State of the Art

Over the last two decades, minimally invasive surgery has become the standard for many types of surgeries which were previously accomplished through open surgery. Minimally invasive surgery generally involves introducing an optical element (e.g., laparoscope or endoscope) through a surgical or natural port in the body, advancing one or more surgical instruments through additional ports or through the endoscope, conducting the surgery with the surgical instruments, and withdrawing the instruments and scope from the body. In laparoscopic surgery (broadly defined herein to be any surgery where a port is made via a surgical incision, including but not limited to abdominal laparoscopy, arthroscopy, spinal laparoscopy, etc.), a port for a scope is typically made using a surgical trocar assembly. The trocar assembly often includes a port, a sharp pointed element (trocar) extending through and beyond the distal end of the port, and at least in the case of abdominal laparoscopy, a valve on the proximal portion of the port. Typically, a small incision is made in the skin at a desired location in the patient. The trocar assembly, with the trocar extending out of the port is then forced through the incision, thereby widening the incision and permitting the port to extend through the incision, past any facie, and into the body (cavity). The trocar is then withdrawn, leaving the port in place. In certain circumstances, an insufflation element may be attached to the trocar port in order to insufflate the surgical site. An optical element may then be introduced through the trocar port. Additional ports are then typically made so that additional laparoscopic instruments may be introduced into the body.

Trocar assemblies are manufactured in different sizes. Typical trocar port sizes include 5 mm, 10 mm and 12 mm (available from companies such as Taut and U.S. Surgical), which are sized to permit variously sized laparoscopic instruments to be introduced therethrough including, e.g., graspers, dissectors, staplers, scissors, suction/irrigators, clamps, forceps, biopsy forceps, etc. While 5 mm trocar ports are relatively small, in some circumstances where internal working space is limited (e.g., children), it is difficult to place multiple 5 mm ports in the limited area. In addition, 5 mm trocar ports tend to limit movements of instruments inside the abdominal cavity to a great extent.

Further, while laparoscopic surgery has reduced the trauma associated with various surgical procedures and has concomitantly reduced recovery time from these surgeries, there always remains a desire in the art to further reduce the trauma to the patient.

One area of trauma associated with laparoscopic surgery identified by the inventor hereof as being susceptible of reduction are the scars which result from the trocar ports used. In many laparoscopic surgeries, three or more trocar incisions are made. For example, in laparoscopic hernia repair surgery, four trocar incisions are typically made, with one incision for insufflating the abdomen and inserting the optical device, two incisions for trocar ports for inserting graspers therethrough, and a fourth port for passing a stapler therethrough. Those skilled in the art and those who have undergone surgical procedures recognize that even the 5 mm trocar ports leave holes which must be stitched and which result in scars.

A second area of trauma associated with laparoscopic surgery identified by the inventor hereof as being susceptible of reduction relates to trauma resulting from the manipulation (angling) of the trocar ports required in order to conduct the surgery due to inexact placement. Angling of the port can cause tearing at the incision periphery.

Those skilled in the art will also appreciate that because of the number of trocar assemblies and laparoscopic tools used in laparoscopic surgery (most of which are disposable because of the cost and complications associated with autoclaving), the cost of laparoscopic surgery is high. Thus, there always remains a desire in the art to provide lower cost laparoscopic tools.

SUMMARY

It is therefore an object of the invention to provide a minimally invasive surgical assembly which reduces trauma to the patient relative to presently used systems.

It is another object of the invention to provide a minimally invasive surgical assembly which is simple and inexpensive relative to presently used systems.

It is a further object of the invention to provide a minimally invasive surgical assembly which utilizes a 3 mm or smaller incision/port device.

It is also an object of the invention to provide a minimally invasive surgical assembly which will not scar a patient.

It is an additional object of the invention to provide a minimally invasive surgical assembly utilizing effective surgical instruments which are inserted into a 3 mm or smaller port device.

It is still another object of the invention to provide a minimally invasive surgical assembly with reduced number of parts.

In accord with these objects, which will be discussed in detail below, a minimally invasive surgical assembly according to the invention broadly includes an outer hollow needle which has an outer diameter of substantially 2.5 mm (the term "substantially", for purposes of this application meaning .+−.20%), and preferably a diameter of 2.5 mm or smaller and a coaxial surgical instrument having a shaft which extends through the outer hollow needle. The coaxial surgical instrument includes end effectors at the end of the shaft which are biased to an open position such that when the end effectors of the surgical instrument extend out of the needle they open, and they are closed by relative movement of the needle over them. The assembly preferably includes a first fixing element which is used to fix the relative location of the surgical instrument and the needle. The assembly also preferably includes a second fixing element which moves relative to the needle and is located on the outside thereof and which is used to fix the relative location of the needle to the patient. The second fixing assembly may include an anchoring element which permits the needle to be held at different angles relative to the patent According to an embodiment of the invention, the surgical instrument and needle are sized to a very small controlled clearance therebetween so that at least a portion of the shaft of the surgical instrument slides against the inner surface of the needle, thereby forming a seal which is effective against desufflation.

According to another embodiment of the invention, the surgical assembly includes a safety mechanism which prevents inadvertent withdrawal of the end effectors of the surgical instrument totally within the needle such that the needle tip will be "exposed" (i.e., will not have the end effectors extending slightly outward therefrom). The safety mechanism preferably includes an override means so that the assembly can be initially placed in an "armed" position with the needle tip exposed for purposes of initial puncture, as well as for purposes of re-arming.

The surgical assembly of the invention may be used during laparoscopic surgery instead of using an extra trocar and laparoscopic instrument. In particular, with the surgical instrument (e.g., grasper) partially inserted in the needle (i.e., with the end effectors at least partially withdrawn inside the needle) and optionally locked relative to each other by the first fixing element, the needle is used to puncture the skin and advance into the body (e.g., the abdomen). At a desired location (typically under guidance of an already inserted scope), the movement of the needle is stopped. The surgical instrument is then unlocked (if previously locked) and advanced until the end effectors extend past the needle and open to their neutral stress position. The needle and surgical instrument may then further advanced until the end effectors extend over a structure in the body. Then, with the surgical instrument stationary, the needle is advanced relative to the surgical instrument to force the end effectors closed, thereby securely grasping the structure. The first fixing element may then be used to fix the needle relative to the surgical instrument to prevent release of the grasped structure. If desired, the needle with the surgical instrument fixed relative thereto and grasping the structure may be manipulated relative to the body wall (e.g., to lift, push, or otherwise move the structure). When the needle (or the grasped structure) is in a desired location in the body, the second fixing element is slid along the needle and into engagement with the skin of the patient, thereby fixing the grasping end effectors at a desired location in the body. At any time, the grasped structure can be released by causing the first fixing element to release the surgical instrument and then moving the needle backward (proximally) relative to the surgical instrument, thereby permitting the end effectors to reopen. The surgical assembly can be pulled out of the body (preferably with the surgical instrument first moved backward relative to the needle to retract and close the end effectors and locate them inside the needle) leaving just a small puncture mark which will often heal without a scar.

The surgical assembly of the invention thereby accomplishes the objects of the invention with a minimum number of parts and may be used to replace expensive trocar assemblies and laparoscopic instruments.

Additional objects and advantages of the invention will become apparent to those skilled in the art upon reference to the detailed description taken in conjunction with the provided figures.

BRIEF DESCRIPTION OF THE DRAWINGS

FIG. 1 is an enlarged broken cross sectional view of a first embodiment of the surgical assembly of the invention with the end effectors of the surgical instrument in an open (advanced) position.

FIG. 2 is an enlarged broken cross sectional view of a first embodiment of the surgical assembly of the invention with the end effectors of the surgical instrument in a closed (retracted) position.

FIG. 4 is a representation of a first embodiment of an anchoring element for fixing the location of the surgical assembly relative to the patient.

FIGS. 5A and 5B are respective top and side views of another embodiment of an anchoring element for fixing the location of the surgical assembly relative to the patient.

FIGS. 7A-7G are representations of seven different end effectors for the surgical instrument of the invention.

FIG. 10 is a front view of a thumb hold of a surgical instrument.

FIGS. 11A-11C are three views of a plunger which couples the thumb hold and shaft of a surgical instrument.

FIG. 20A is a perspective view of the complete assembly extending through a second fixing element.

FIGS. 21A-21D are an exploded view, an assembled view, a top view, and a cross-sectional view of a third embodiment of the second fixing means of the invention.

FIG. 21E is a bottom view of the body of FIGS. 21A-21D.

FIG. 21F is a perspective view of the squeezable ball of FIGS. 21A-21D.

DETAILED DESCRIPTION

Figure 3A:
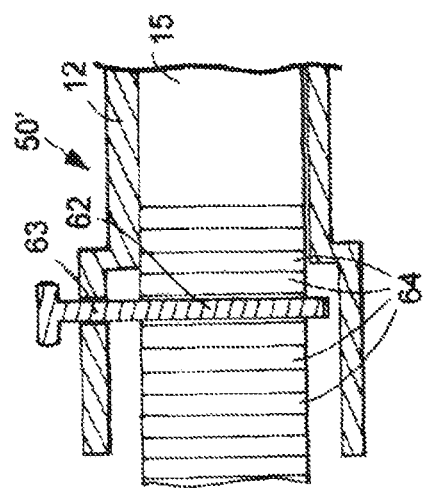
FIGS. 3A-3E are broken representations of five different fixing element systems for fixing the shaft of surgical instrument relative to the needle.

A minimally invasive surgical assembly 10 according to the invention and as seen in FIGS. 1 and 2 broadly includes an outer hollow needle 12 which has an outer diameter of substantially 2.5 mm (0.1 inches), and a coaxial surgical instrument 14 having a shaft 15 which extends through the outer hollow needle. The needle 12 has a sharpened distal end 18 which is angled at about 35.degree. relative to a longitudinal axis of the needle, and a proximal end having a knob or handle 20 for holding and manipulation of the needle. The inside diameter of the needle is substantially 2.0 mm (0.08 inches) and the wall thickness of the needle is substantially 0.25 mm (0.01 inch). The needle is typically between 10 and 30 cm long, and more typically between 13 and 18 cm long (although other sizes could be used, depending upon the surgery involved, and typically larger for obese patients and smaller for infants and small children), and is preferably made from stainless steel, although other materials could be utilized.

The coaxial surgical instrument 14 shown in FIGS. 1 and 2 is a grasper type instrument and includes end effectors 22 at the distal end of the shaft 15 and a handle or knob 24 at the proximal end of the shaft. The end effectors 22 are formed so that they biased to an open position as seen in FIG. 1, such that when the end effectors 22 of the surgical instrument 14 extend out of the needle 12 they open, and when the needle extends over them as in FIG. 2, they close. The end effectors 22 may be formed from the end of the shaft 15 as described in U.S. Pat. No. 6,616,683 to Toth et al. which is hereby incorporated by reference herein in its entirety, or in any other desired manner such as by forming end effectors and connecting them to the shaft. The shaft 15 of the surgical instrument 14 must be long enough to permit the end effectors to extend out of the needle as seen in FIG. 1. The surgical instrument 14 is preferably made from stainless steel, although other materials could be utilized for all or part of the instrument 14.

More particularly, in one embodiment, where the surgical instrument is to be used for grasping, (i.e., the end effectors are graspers as shown, e.g., in FIGS. 1, 7A-7F, 8A-8D and 17), the graspers can be formed from sixty percent cold reduction Custom 475 precipitation-hardenable martensitic stainless steel wire available from Carpenter Specialty Wire Products, Orangeburg, S.C. The stainless steel wire is described in U.S. Pat. No. 6,630,103 which is hereby incorporated by reference herein in its entirety and includes 9.0%-13.0% and more preferably 10.5-11.5% chromium, 5.0%-11.0% and more preferably 8.0%-9.0% cobalt, 7.0%-9.0% and more preferably 7.5%-8.5% nickel, 3.0%-6.0% and more preferably 4.75%-5.25% molybdenum, 1.0%-1.5% and more preferably 1.1%-1.3% aluminum, 1.0% and more preferably 0.005-0.05% titanium (maximum), 0.5% and more preferably 0.1% silicon (maximum), 0.75% and more preferably 0.25% copper (maximum), 0.5% and more preferably 0.1% manganese (maximum), 0.025% and more preferably 0.0025% sulfur (maximum), 0.03% and more preferably 0.015% carbon (maximum), 1.0% and more preferably 0.20% niobium (maximum), 0.04% and more preferably 0.015% phosphorus (maximum), 0.03% and preferably 0.01% nitrogen (maximum), 0.02% and preferably 0.003% oxygen (maximum), 0.01% and preferably 0.0015-0.0035% boron, and remainder iron. The wire may be subject to an EDM procedure to form the end effectors as approximately 1.8 mm graspers with teeth (e.g., as shown in FIG. 7G—169a, and FIG. 17—569) or other structures, and then subject to precipitation age hardening heat treatment at typically 975.degree. F. for an hour. The resulting end effectors have a high yield strength, typically in excess of 300,000 psi, with good elongation and toughness. This provides a clinical advantage in that when too much material is placed in the end effectors and the end effectors are actuated, the jaws will neither crush the material, nor fracture themselves, but will plastically deform.

According to one aspect of the preferred embodiment of the invention, the surgical instrument 14 and needle 12 are sized so that at least a portion of the shaft 15 of the surgical instrument 14 slides against the inner surface of the needle 12, thereby forming a seal which is effective against desufflation. Thus, where the inner diameter of the needle is 2.00 mm, the outer diameter of the shaft 15 is approximately 1.99 mm (0.078 inches), or about 0.01 mm smaller than the inner diameter of the needle. This small difference in diameters results in a sliding low clearance fit which can be felt as a drag and which effectively acts as a seal against desufflation. If desired, only a portion of the shaft be sized to interferingly slide against the inner surface of the needle. Alternatively, the needle may include an internal gasket or seal or grease which seals against the outer diameter of the shaft.

Turning to FIGS. 3A-3E, according to the preferred embodiment, the assembly 10 of the invention includes a first fixing mechanism, element, or system which is used to fix the relative location of the surgical instrument 14 and the needle 12. In FIG. 3A, the first fixing system 50 is shown to include notches 52 on the shaft 15 of the surgical instrument 14, and a screw 54 which extends through a threaded radial hole 55 in the needle 12 or its handle. When it is desired to fix the surgical instrument 14 relative to the needle 12, the screw 54 is screwed (typically clockwise) into the needle and into engagement with a notch 52. When it is desired to release the surgical instrument 14, the screw 54 is unscrewed so that it is no longer engaged in the notch. It will be appreciated that instead of a screw 54 and a threaded radial hole 55, a spring loaded pin which extends through a radial hole in the needle (or needle handle) could be utilized to lock the surgical instrument 14 relative to the needle 12.

Figure 3B:
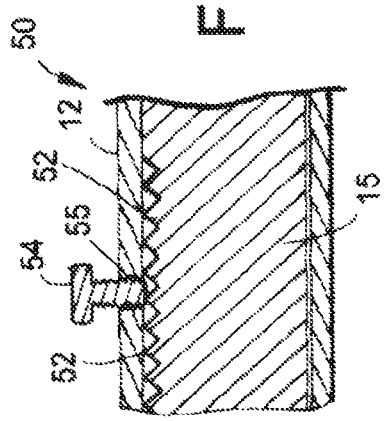

In FIG. 3B, a second fixing system 50' is shown to include radial grooves 60 on the shaft 15 of the surgical instrument and a clip 61 having spring arms 62 (one shown), and a shaft 63. The shaft 63 of the clip 61 extends through a wall of the needle or, more preferably, its handle, and the spring arms 62 engage a radial groove 64 on the shaft 15. When the shaft 15 of the needle is pushed or pulled relative to the needle, the spring arms 62 spread to permit movement of the shaft 15 past the clip 61. It will be appreciated that if the spring arms 62 are sufficiently springy, grooves are not required on the shaft 15 of the needle as the spring arms 62 will firmly hold the shaft in position.

Figure 3C:
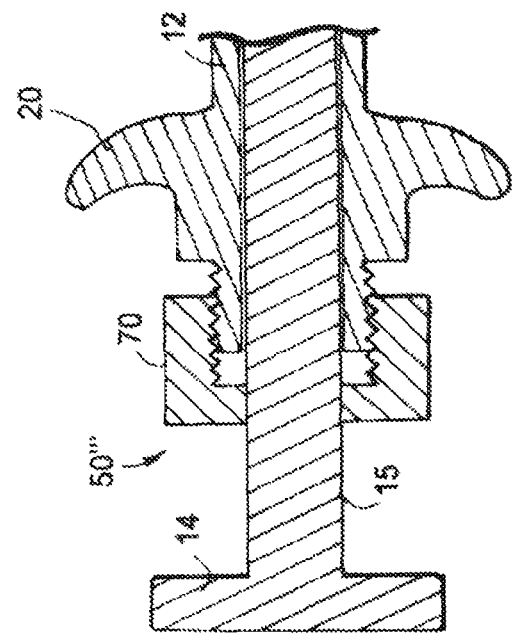

A third fixing system 50" is seen in FIG. 3C and includes a plastic screw 65 which extends around the shaft 15 of the surgical instrument 14, and an inner thread 66 located on the handle or knob 20 of the needle 12. When it is desired to fix the surgical instrument 14 relative to the needle 12, the screw 65 is screwed into the threaded handle or knob needle 20 of the needle 12. The plastic screw 65 and the inner thread 66 of the handle or knob 20 of the needle are sized to cause the plastic screw 65 to deform and tighten around the shaft 15 when the screw 65 is screwed into the thread 66, thereby fixing the locations of the needle 12 and surgical instrument 14 relative to each other. When it is desired to release the surgical instrument 14, the screw 65 is unscrewed sufficiently to permit movement of the surgical instrument relative to the needle. As will be appreciated by those skilled in the art, the screw 65 may have a gripping member such as a head (not shown) to help the practitioner apply torque.

Figure 3D:
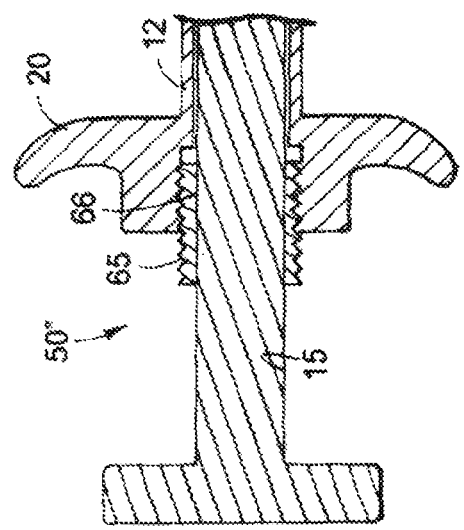

FIG. 3D shows a fourth fixing system 50''' which includes a thumb screw 70 and a handle portion 20 of the needle 12 which includes a thread (not shown), and which is flexible or plastic. In particular, the thumb screw 70 when screwed onto the handle portion threads causes the handle portion to clamp down on the shaft 15 of the surgical instrument 14 and lock the surgical instrument relative to the needle.

Figure 3E:
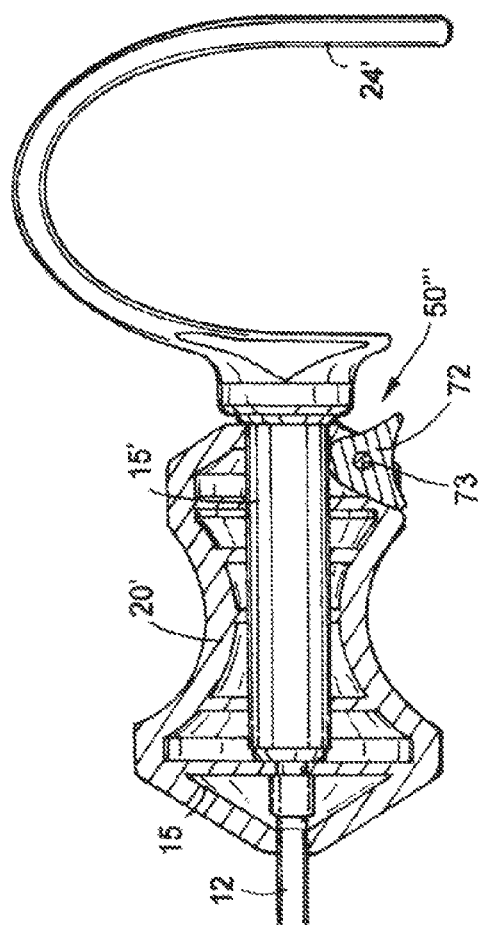

A fifth fixing system 50'''' is seen in FIG. 3E where a cam element 72 is rotatingly coupled to the needle handle 20' by a pin 73. When in a first orientation, the cam element 72 permits a rear portion 15' of the shaft 15 of the surgical instrument 14 to move in an uninhibited manner. When in a second orientation as shown in FIG. 3E, the cam element 72 engages the rear portion 15' of the shaft 15 and holds it fixed relative to the needle handle 20' and needle 12. It will be appreciated that in addition to the fixing system 50'''' which is different the fixing systems of FIGS. 3A-3D, the needle handle 20' and surgical instrument handle 24' are modified relative to the handles 20, 24 shown in FIGS. 1 and 2 and FIGS. 3A-3D.

The assembly also preferably includes a second fixing element which moves relative to the needle and is located on the outside thereof and which is used to fix the relative location of the needle to the patient. More particularly, as seen in FIG. 4, the second fixing element is a soft plastic suction cup 80 which engages and is frictionally slidable over the outer surface of the needle 12, and which can be pressed against the abdominal wall of a patient to cause a suction connection. If desired, the outer surface of the needle 12 may be provided with mating elements such as bumps, serrations, or grooves (not shown), and the suction cup 80 may be provided with a reciprocal mating element (not shown) for engaging the mating element of the outer surface of the needle 12 to more strongly fix the location of the suction cup 80 relative to the needle 12.

Turning to FIGS. 5A and 5B, a second embodiment of the second fixing assembly is seen to include a plastic suction cup 80' having a top proximal hole 82 and a plurality of bayonet-type grooves 84 through which the needle 12 can be maneuvered. The suction cup 80' thereby permits the needle 12 to be held at different angles relative to the patient.

Figure 6:
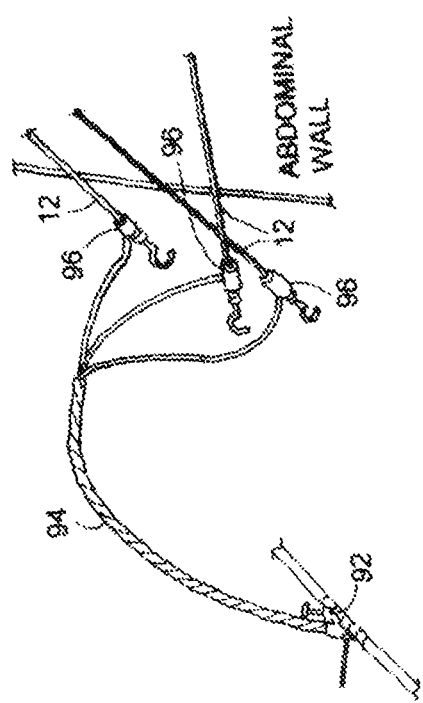
FIG. 6 is a schematic view of another mechanism fixing the location of the surgical assembly relative to the patient.

In lieu of a suction cup, it is possible to fix the location of the needle 12 and surgical instrument 14 relative to the patient by using standard equipment and modifying the surgical assembly of the invention slightly. Thus, as seen in FIG. 6, a standard multiheaded clip 90 is provided which is fixed by a clamp 92 to the side of an operating room table. The multiheaded clip 90 includes a malleable metal rod 94 and a plurality of clip elements 96. The surgical assembly 10 may then be held in a desired position relative to the patient by providing the needle 12 or surgical instrument 14 with a clip receiver or groove which may be located on the outside surface of the needle handle or on the handle or knob of needle or surgical instrument. Details of a presently preferred multiheaded clip can be found in co-owned U.S. Ser. No. 11/668,169 filed Jan. 29, 2007 and entitled "Platform for Fixing Surgical Instruments During Surgery".

Figure 7F:
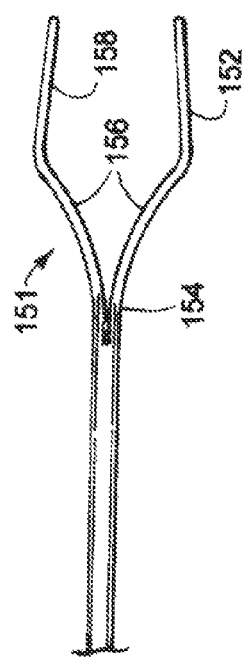

As will be appreciated by those skilled in the art, the surgical instrument 14 of the invention may take various forms. Thus, FIGS. 7A-7G show representations of seven different end effectors for the surgical instrument of the invention (although others could be utilized). FIG. 7A shows a detailed view of a grasper such as seen in FIGS. 1 and 2. The grasper end effectors 101 include two arms 102 which extend from shaft 15, each of which is approximately 19 mm (0.75 inch) long. The arms are slightly rounded on their outer peripheries in the same profile as the shaft 15, with each rounded surface forming an arc of between forty-five and ninety degrees. The first portions 104 (e.g., about 4 mm) of the arms are relatively straight in their at rest open position. The middle portions 106 of the arms 102 then angle away from each other (each at between 6.degree. and 18.degree. from the horizontal) until they extend approximately 7 mm apart from each other. In order to provide a good spring load, the middle portions of the arms may be reinforced with or formed from spring steel. The tips 108 (e.g., approximately 3 mm) of the arms are then bent back to parallel the first portions 104. Their outer surfaces may also be flattened.

If desired, the grasper of FIG. 7A can be formed from a solid rod or a tube of steel, by cutting the end of the tube in half to form arms (e.g., via use of a laser or an EDM machine), further removing material from the underside of each arm at the first portions 104, and then bending the arms at the intersections of the first portions 104 and middle portions 106, and at the intersections of the middle portions 106 and tips 108.

FIG. 7B is a representation of lung clamp end effectors 111. The lung clamp end effectors extend from the shaft 15 with arms 112 which terminate in loops 114 which define openings 115. While not shown in detail in FIG. 7B, the arms 112 are similar to the arms of the grasper of FIG. 7A in that they are slightly rounded on their outer peripheries in the same profile as the shaft 15, include first portions 116 which are relatively straight in their at rest open position and middle portions 118 which angle away from each other until they extend approximately 6 mm apart from each other. The loops 114 are then bent back to parallel the first portions 116. In order to provide a good spring load, the middle portions of the arms may be reinforced with or formed from spring steel.

FIG. 7C is a representation of hybrid end effectors 121 including one grasper 122 and one lung clamp 123. The grasper 122 is substantially as described above with reference to FIG. 7A, and the lung clamp 123 is substantially as described above with reference to FIG. 7B.

FIG. 7D is a representation of non-crushing clamping end effectors 131 including one grasper 132 and a rubber covered arm 133.

FIG. 7E is a representation of retractor end effectors 141. The retractor end effectors 141 are formed from wire mesh elements 143 which at rest are substantially flat, but which are bent into an arcuate shape when retracted into the needle.

FIG. 7F is a representation of a grasper similar to that of FIG. 7A. The primary differences between the grasper end effectors 151 of FIG. 7F and the grasper end effectors 101 of FIG. 7A are that the arms 152 are each approximately 25 mm-35 mm (1-1.38 inch) long, the middle portions 156 angle away from each other at about 50.degree. or 25.degree. from the horizontal. The tip portions 158 shown in FIG. 7F are approximately 12 mm long and bend back slightly beyond being parallel to the first portions 154 so that they are angled slightly toward each other. Alternatively, the tip portions need not bend back beyond the parallel or even at all. If the tip portions are not bent back, the tip portions may be designed to open 15 mm-20 mm relative to each other.

Figure 7G:
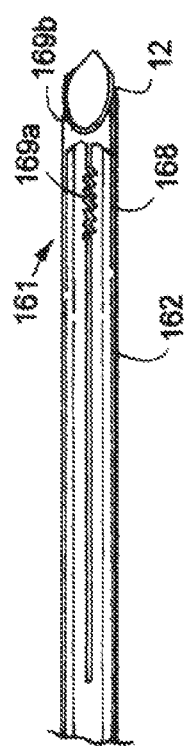

FIG. 7G is a representation of a crushing grasper 161 shown in a closed position within a needle 12. The crushing grasper 161 is similar to the grasper 101 of FIG. 7A except that it is slightly longer (approximately 22 mm long), and the tip portions 168 have teeth 169a and have a rounded front 169b such that they present a blunt almost hemispherical surface. When the end effectors 161 of FIG. 7G are moved forward relative to the needle 12, they preferably remain in a closed position until approximately half the length of the arms 162 extend beyond the needle. Thus, as will be discussed below, the end effectors of the surgical instrument 14 may act as an obturator relative to the needle to guard the needle from causing accidental needle tip trauma.

The surgical assemblies of the invention may be used during laparoscopic surgery instead of using extra trocars and laparoscopic instruments. In particular, with the surgical instrument 14 (e.g., grasper end effectors 111) partially inserted in the needle 12 (i.e., with the end effectors withdrawn at least partially inside the needle) and optionally locked relative to each other by the first fixing element (e.g., fixing system 50), the needle 12 is used to puncture the skin and advance into the body (e.g., the abdomen). At a desired location (typically under guidance of an already inserted scope), the movement of the needle is stopped. The surgical instrument 14 is then unlocked (if previously locked) and advanced until the end effectors 111 extend past the needle 12 and open toward their neutral stress position. The needle and surgical instrument may then further advanced until the end effectors extend over a structure in the body. Then, with the surgical instrument stationary, the needle is advanced relative to the surgical instrument to force the end effectors 111 closed, thereby securely grasping the structure. The first fixing element or system (e.g., system 50) may then be used to fix the needle relative to the surgical instrument to prevent release of the grasped structure. If desired, the needle with the surgical instrument fixed relative thereto and grasping the structure may be manipulated relative to the body wall (e.g., to lift, push, or otherwise move the structure). When the needle (or the grasped structure) is in a desired location in the body, the second fixing element (e.g., 80) is slid along the needle and into engagement with the skin of the patient, thereby fixing the grasping end effectors at a desired location in the body. At any time, the grasped structure can be released by causing the first fixing element to release the surgical instrument and then moving the needle backward relative to the surgical instrument, thereby permitting the end effectors to reopen. The surgical assembly can be pulled out of the body (preferably with the surgical instrument first moved backward at least partially relative to the needle to retract and close the end effectors) leaving just a small puncture mark which will often heal without a scar.

It is noted that because of the small diameter of the surgical assembly, withdrawal of the needle assembly from the abdomen will not cause desufflation, and should not require stitching to close the wound. It is also noted that because of the small diameter of the surgical assembly the elimination of a trocar port, the surgical assembly can be easily moved in any direction (i.e., it can be easily angled) during surgery.

The surgical assembly of the invention thereby accomplishes the objects of the invention with a minimum number of parts and may be used to replace expensive trocar assemblies and laparoscopic instruments.

Figure 8A:
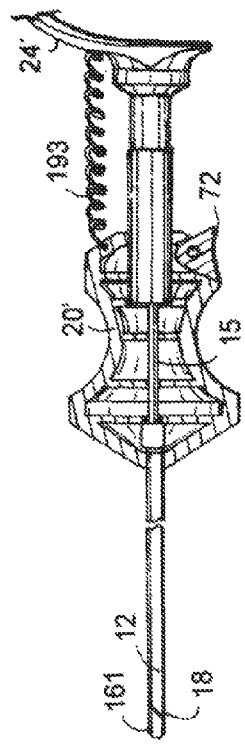
FIG. 8A-8D are representations of a modified surgical instrument having end effectors acting as an obturator, and with the end effectors located in a rest shielding position, a puncturing position, an extended position, and a withdrawn position respectively.
Figure 8B:
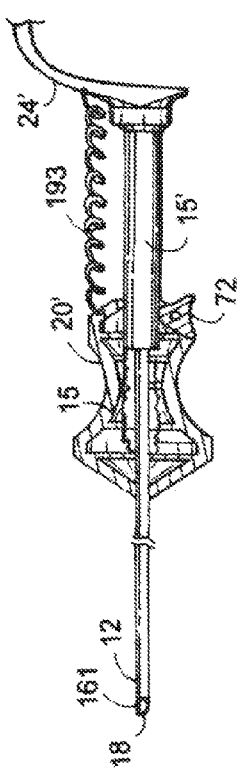
Figure 8C:
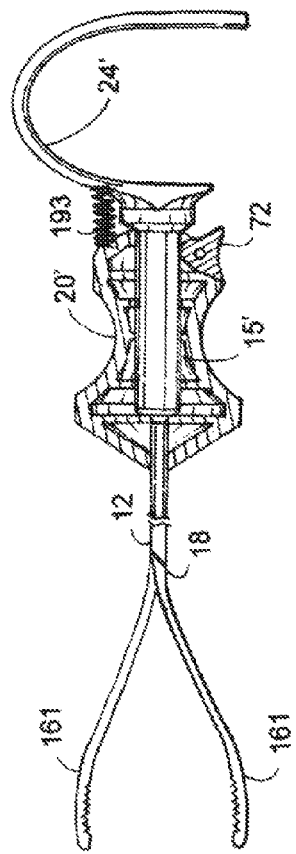
Figure 8D:
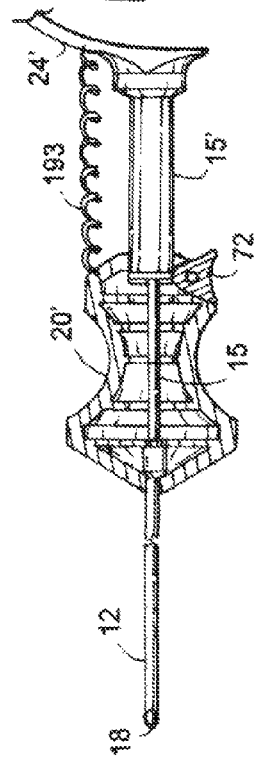

According to another aspect of the invention, as previously mentioned, the tips of the end effectors of the surgical instrument may be used to function as an obturator. Thus, as seen in FIGS. 8A-8D, a surgical assembly combining aspects seen in FIGS. 3E and 7G is shown, except that a spring 193 is provided and coupled to the handles 20', 24' of the needle and surgical instrument respectively. Spring 193, in an at rest position, causes the rounded end effectors 161 to assume a position where the end effectors extend out of the needle 12 but remain in a closed position as seen in FIG. 8A. In this partially extended position, the end effectors 161 act as an obturator or protection from accidental needle tip trauma. When the surgical assembly is used to puncture skin as seen in FIG. 8B, pressure is placed on the end effectors, thereby causing the end effectors 161 to be pushed back into and thereby exposing the needle, and causing the surgical instrument to move backward relative to the needle, thereby placing spring 193 under tension. When the skin is punctured and the needle extends into a cavity and pressure on the end effectors is released, the spring 193 pushes the surgical instrument forward to reassume the position of FIG. 8A. When it is desired to extend the end effectors 161 to grasp a structure, the surgical instrument may be pushed forward relative to the needle as seen in FIG. 8C, thereby placing the spring 193 under compression, and opening the end effectors 161. The end effectors may then be closed over the object by pulling end effectors backward relative to the needle whereby the needle acts on the end effectors to at least partially close them, with the spring 193 assuming a partially compressed position. The grasping position (and any other position) may be locked at any time using the fixing element (e.g., cam 72). If it is desired to pull the end effectors totally into the needle as seen in FIG. 8D, that may be accomplished by pulling the surgical instrument backward relative to the needle, again placing the spring 193 in tension. The surgical instrument can be locked in that position using the fixing element.

Figure 9A:
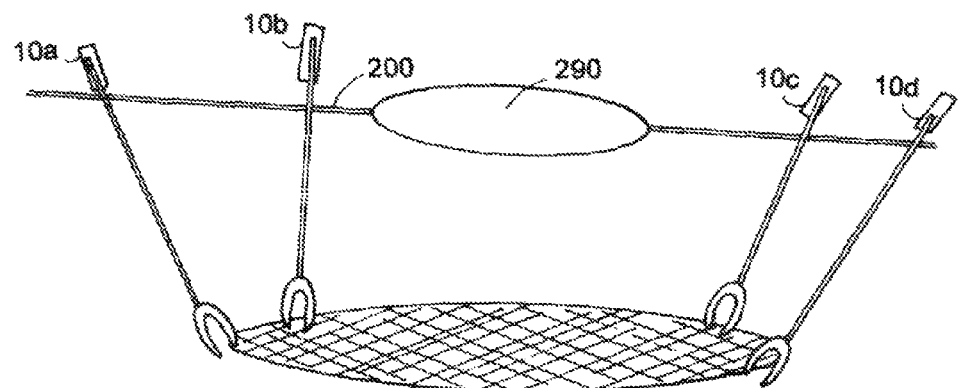
FIGS. 9A-9D are schematic diagrams showing the use of four surgical assemblies of the invention being used for a hernia repair operation.
Figure 9B:
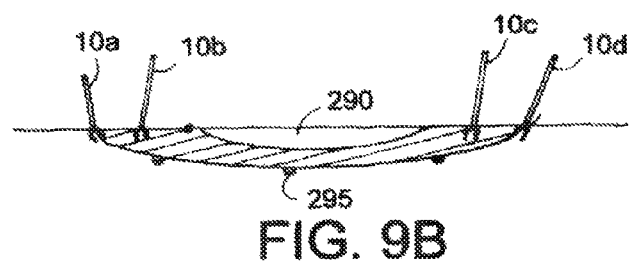
Figure 9C:
Figure 9D:
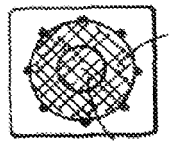

Use of a plurality of surgical assemblies 10a-10d is seen in FIGS. 9A-9D with respect to a hernia repair operation. In particular, an abdominal wall 200 is seen with a hernia (opening) 290. The hernia 290 is to be repaired with mesh 290 which has been inserted into the abdomen under guidance of a laparoscope (not shown). As seen in FIG. 9A, four surgical assemblies 10a-10d according to the invention have been used to pierce the abdominal wall. The four assemblies 10a-10d are then used to grasp corner areas of the mesh 295 by moving the grasper end effectors out of their respective needles and over and around the mesh corners, and by moving the needles forward relative to the grasper instruments to force the end effectors closed over the mesh. The needles and surgical instruments are then preferably locked relative to each other (using first fixing mechanisms or systems such as discussed above with reference to FIGS. 3A-3E), and the assemblies 10a-10d are pulled upward to cause the mesh 295 to lie directly below the hernia 290 as seen in FIG. 9B. The assemblies are then preferably locked in place relative to the abdominal wall using mechanisms such as discussed above with reference to FIGS. 4, 5A, 5B, and 6. Then, using a laparoscopic stapler (not shown) typically introduced through a standard trocar port, the mesh is stapled in place. The mesh may then be released by the assemblies 10a-10d by unlocking the surgical instruments, unlocking the second fixing mechanisms, and moving the respective needles backward in order to open the end effectors. After the mesh is released, the end effectors of the surgical instruments are withdrawn at least partially into the needles (and optionally locked in place), and withdrawn from the abdomen, leaving the mesh 295 stapled in place as seen in FIGS. 9C and 9D.

It will be appreciated by those skilled in the art that the minimally invasive surgical assemblies of the invention can be used for various other surgical procedures, including but not limited to tuboplasty, gastric bypass, bowel connection, kidney surgery, appendectomy, menisectomy, discectomy, etc. The minimally invasive surgical assemblies of the invention also have particularly advantageous use in neo-natal and pediatric surgeries, and the assemblies and methods can be used on animals or cadavers.

Figure 20B:
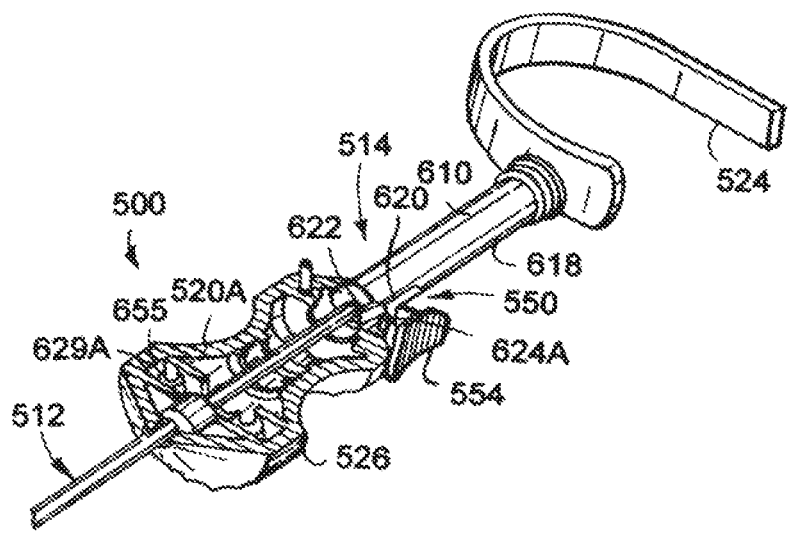
FIG. 20B is a perspective view of a proximal portion of the assembly with only part of a housing shown.

Another embodiment of the surgical assembly of the invention is shown in FIGS. 10-20B. As seen in FIGS. 20A and 20B, the assembly 510 includes a needle 512 and a medical instrument 514. The needle has a sharpened distal tip 518 and a handle 520. The medical instrument has end effectors 522 and a handle 524. Also shown in FIGS. 20A and 20B is a lever 554 of a safety lock mechanism 550 which also serves as a first fixing mechanism. Seen in FIG. 20A is a second fixing assembly 800 discussed hereinafter with reference to FIGS. 21A-21G. Details of the needle 512, the medical instrument 514, and the safety lock mechanism 550 and the functioning of the safety lock mechanism are seen in FIGS. 10-20B.

The handle 520 of the medical instrument is seen in FIG. 10. Handle 524 includes a loop 601 which is sized to receive the thumb of a practitioner and a post 603 which extends in a direction parallel or coaxial with the shaft of the instrument 514. The post 603 may be provided with a seat 605 which can be used to receive a pin 607 (FIG. 16D) which will fix the handle 520 relative to the remainder of the medical instrument 514 as discussed below.

The post 603 of the handle 524 is received in a plunger 610 shown in FIGS. 11A-11C. More particularly, plunger 610 is a cylindrical member having a head 611 and defining a top tubular opening 612, a pin hole 613, a bottom tubular opening 614, a shaft surface 615 defining a first groove 616 which stops at a stop surface 617, a second groove 618, a flattened distal portion 620 which helps define a stop surface 621 for groove 618, and a bevel 622. The top opening 612 receives the post 603 of the handle 520, and a pin 607 (FIG. 16D) is inserted in pinhole 613 so as to engage the seat 605 of the post 603. The pinhole 613 is eccentric relative to the post 603 so that it engages seat 605 and fixes the handle 524 axially relative to the plunger 610, but permits the handle 524 to rotate relative to the plunger. The bottom tubular opening 614 is provided for receiving the shaft 515 of the medical instrument (the top portion of which is shown only in FIG. 11B). If desired, the plunger 610 can be formed as a cylinder with a single passageway defining openings 612 and 614.

The grooves 616 and 618 defined in the shaft surface 615 of the plunger 610 are used to perform several functions. As will be described in more detail hereinafter, groove 616 is used to fix the orientation of the end effectors 522 of medical instrument 514 relative to the bevel of the tip of the needle 512. The stop surface 617 at the end of groove 618 also prevents the medical instrument 514 from being completely removed from the needle 512. Groove 618, together with flattened portion 620, stop surface 621, and bevel 622 work together with lever 554 (FIGS. 14 and 20) to provide a safety lock and a first fixing means 550 for the assembly 500.

Figure 12A:
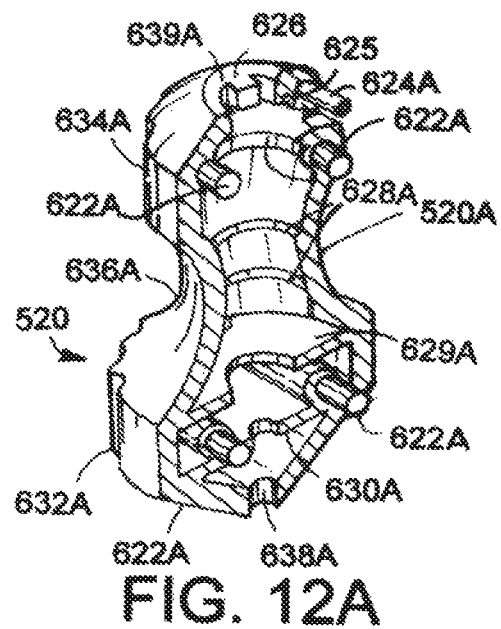
FIGS. 12A-12B are perspective views of the inside and outside of one half of a proximal housing.
Figure 12B:
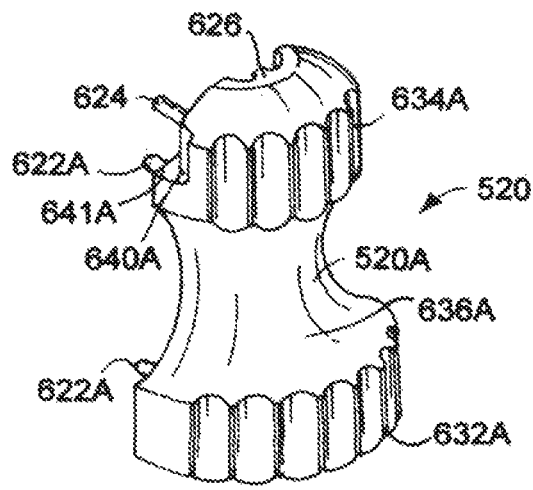
Figure 13A:
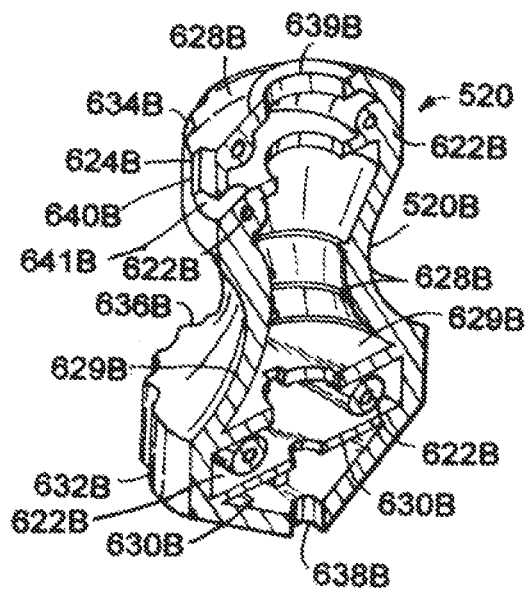
FIGS. 13A-13B are perspective views of the inside and outside of a second half of the proximal housing.
Figure 13B:
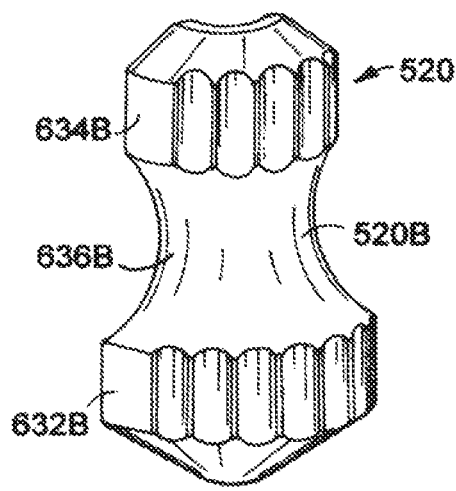

Turning now to FIGS. 12A, 12B, 13A, and 13B, the handle 520 for the needle is seen. The handle 520 is preferably formed from two similar mating parts 520A, 520B which when mated together form generally a spool-shaped handle. As seen in FIGS. 12A and 12B, handle portion 520A includes four internal mating posts 622A, a rotation post 624A, a spring catch or notch 625, a location tongue 626, plunger locating ribs 628A, a needle hub locating rib 629A and a needle shaft locating rib 630A. Portion 520A also has an outer surface with lower and upper ribbed portions 632A, 634A, a smooth hourglass shaped waist 636A therebetween, with the lower ribbed portion 632A defining an opening 638A for the needle shaft, and the upper ribbed portion 634A defining an opening 639A for the plunger. The upper ribbed portion 634A also defines an opening 640A for the lever 554 as will be discussed hereinafter with a stop surface 641A. As seen in FIGS. 13A and 13B, handle portion 520B generally corresponds to handle portion 520A, and with four internal mating post receivers 622B, a rotation post receiver 624B, plunger locating ribs 628B, needle hub locating rib 629B with locating notch 629B1, and a needle shaft location rib 630B. Portion 520B also has an outer surface with lower and upper ribbed portions 632B, 634B, a smooth hourglass shaped waist 636B therebetween, with the lower ribbed portion 632B defining an opening 638B for the needle shaft, and the upper ribbed portion 634B defining an opening 639B for the plunger. The upper ribbed portion 634B also defines an opening 640B for the lever 554 with a stop surface 641B as will be discussed hereinafter.

Figure 14:
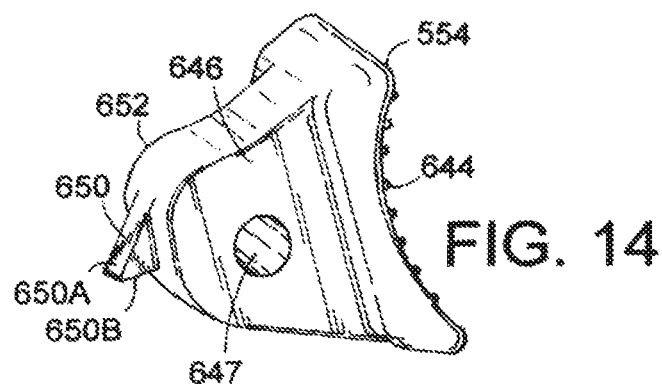
FIG. 14 is a perspective view of a lock mechanism for the surgical instrument.
Figure 18A:
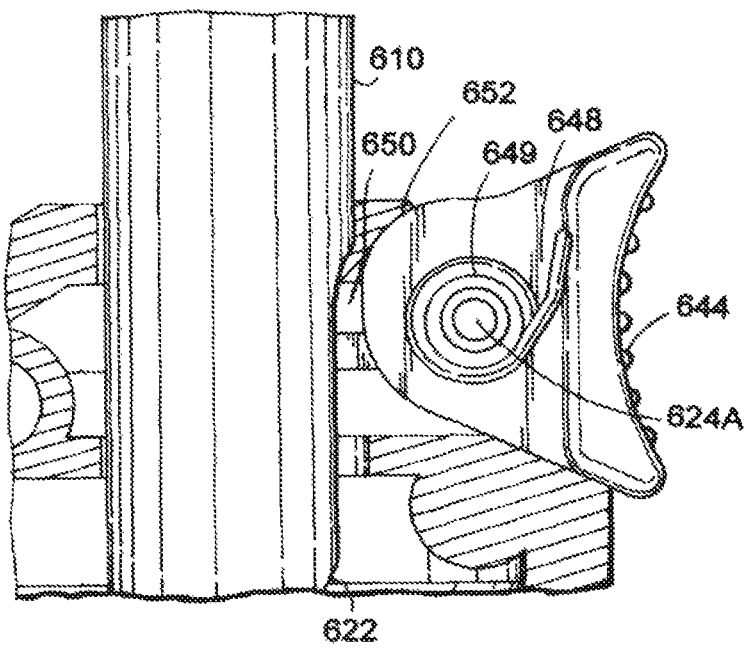
FIGS. 18A-18B are partially transparent side and perspective views showing the lock mechanism engaging the plunger in an unlocked position.
Figure 18B:
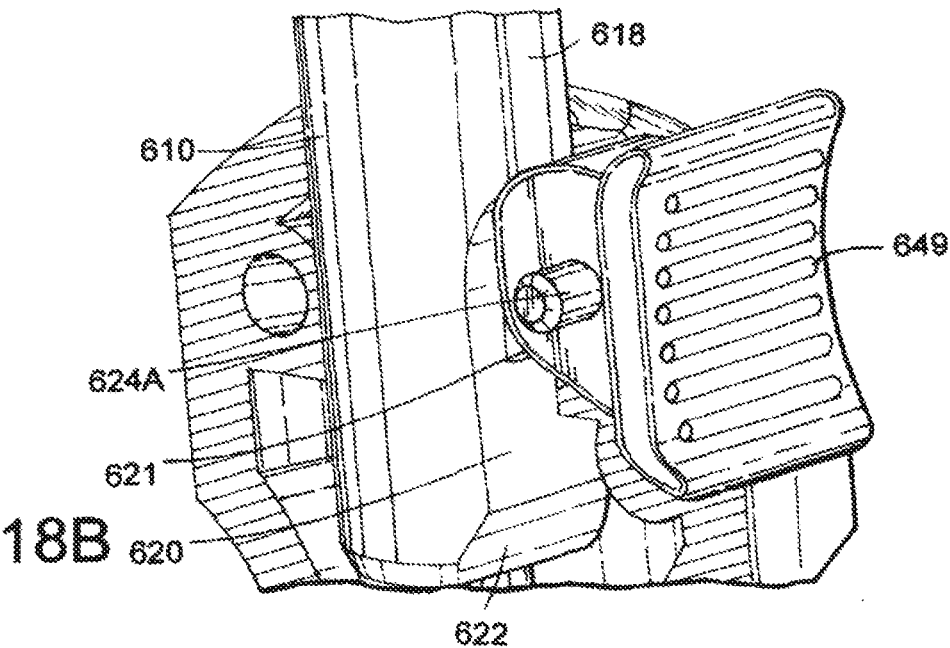

Lever 554 is seen in FIGS. 14, 18A and 18B, and includes a concave ribbed friction surface 644, a body 646 defining a hole 647 and a spring seat 648 (seen in FIG. 18A) for housing a spring 649, and a nose 650. The hole 647 is sized to receive the rotation post 624A such that the lever 554 can rotate about the post. The nose 650 is generally triangular in shape with an angled top surface 650A and a straight bottom surface 650B and has a first width which permits the nose 650 to ride in groove 618 of the plunger. The body 646 has a second larger width which is sized to fit within an opening into the handle formed by openings 640A, 640B. As will be discussed hereinafter, the rounded portion 652 of the body adjacent the top of the nose is used as the first fixing element for the assembly. The friction surface 644 has a preferably a third even larger width and is located outside the mating parts 520A, 520B of the handle.

Figure 15A:
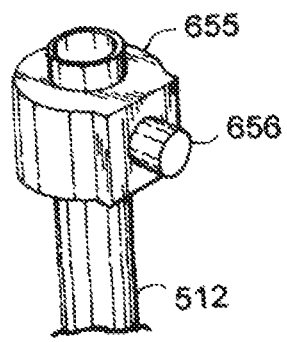
FIG. 15A-15B are perspective views of a needle hub and needle tip.
Figure 15B:
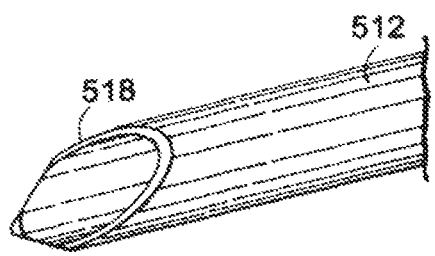

Turning now to FIGS. 15A and 15B, the proximal and distal portions of the needle 512 are seen. More particularly, as seen in FIG. 15B, the distal tip 518 of the hollow needle is beveled and sharp. As seen in FIG. 15A, the proximal end of the hollow needle 512 is provided with a hub 655 with a boss 656. As indicated by FIG. 20B, the hub 655 is sized to be captured in a hole formed by the needle hub receiving ribs 629A and 629B, with the boss 656 received in the cutout 629B1 so as to orient the needle bevel in a desired orientation relative to the handle 520. If desired, the proximal portion of the needle shaft may be textured to provide an extra gripping surface for the practitioner.

Figure 17:
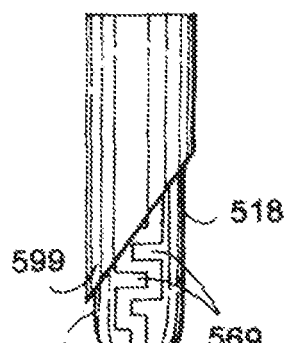
FIG. 17 is a view of the distal end of the surgical assembly with the end effectors assuming a safety position relative to the needle tip.

Prior to discussing the functioning of the plunger 610 and lever 554, a couple of additional aspects of the invention are worth noting. First, the spring seat 648 (FIG. 18) and spring catch or notch 625 (FIG. 12A) are arranged to cause the spring 649 to bias the lever 554 in a clockwise direction into a position where the nose 650 is substantially perpendicular to the perpendicular axis of the plunger 610 and needle 512. Rotation of the lever 554 clockwise from that position is stopped by the surface 641A, 641B of the upper ribbed portions of the spool. Rotation of the lever 554 counterclockwise, against the spring can be accomplished easily by applying a small amount of counterclockwise force to the lever 554. Second, while grooves 616 and 618 are shown in FIGS. 11A-11C to be one hundred eighty degrees apart, they are more preferably ninety degrees apart, and their actual locations must be considered in conjunction with the location of pin 624A (FIG. 12A) which sets the position of the lever 554 and the tongue 626 (FIG. 12A) which rides in groove 616. Third, the orientation of the needle 512 through the use of the needle hub 655 and nub 656 (FIG. 15A) and the needle hub receiving ribs 629A, 629B and locating notch 629B1 is preferably selected relative to the orientation of the end effectors of the surgical instrument 514 (which are fixed relative to the plunger 610) so that the end effectors present themselves in a shielding manner relative to the bevel tip 518 of the needle 512. In particular, according to one aspect of the invention, it is desirable for the end effectors 518 to present as shown in FIG. 17 with the full, typically rounded outer surface 518 of one end effector resting along the very tip 599 of the bevel edge of the needle as opposed to the being rotated relative thereto. In this manner the surface 518 of the end effector effectively continues and/or rounds the beveled surface of the needle, i.e., it acts as an internal shield so that the exposure of the sharpness of the needle is significantly reduced. Fourth, if desired, the distal portion of the plunger 610 (including the flattened portion 620) may be colored with a red or other pigment (not shown) so that it is highly visible as discussed hereinafter.

The functioning of the plunger 610 and the lever 554 in order to provide a safety locking function and a first fixing function is understood best with reference to FIGS. 16-19. More particularly, FIG. 16A shows the positions of the plunger 610 and the lever 554 when the assembly in an "armed" position with the medical instrument 514 fully retracted relative to the needle 512 so that the needle tip 518 is not guarded by the end effectors. In the position of FIG. 16A, the tongue 626 (FIG. 12A) of the spool engages the stop surface 617 (FIGS. 11B and 11C) of the plunger 610. Also, in the position of FIG. 16A, the nose 650 of the lever 554 either doesn't engage the plunger 610 at all, or engages the beveled end 622 of the plunger. In this armed position, the assembly 510 (and in particular the needle 512) can be used to puncture the skin of a patient so that the distal end of the assembly can pass into a body cavity (e.g., the diaphragm). Also, in this position, the distal portion of the plunger 610 extends out of the needle handle 520. If this portion of the plunger is made highly visible with coloration, the practitioner is given a viewable warning that the assembly is armed (i.e., the needle is unshielded).

Figure 16A:
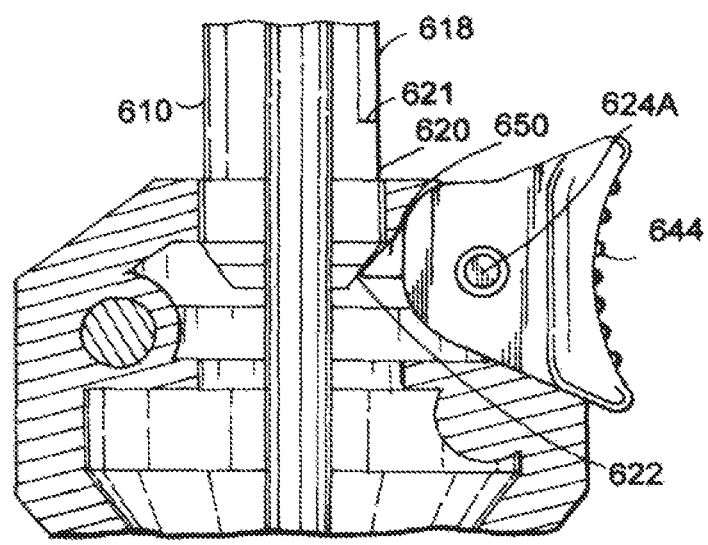
FIGS. 16A-16E are transparent views of the safety/locking mechanism with the plunger in a fully retracted position, a beginning deployment position, a position just prior to reaching a safety locking position, the safety locked position, and a working or operating range position respectively.
Figure 16B:
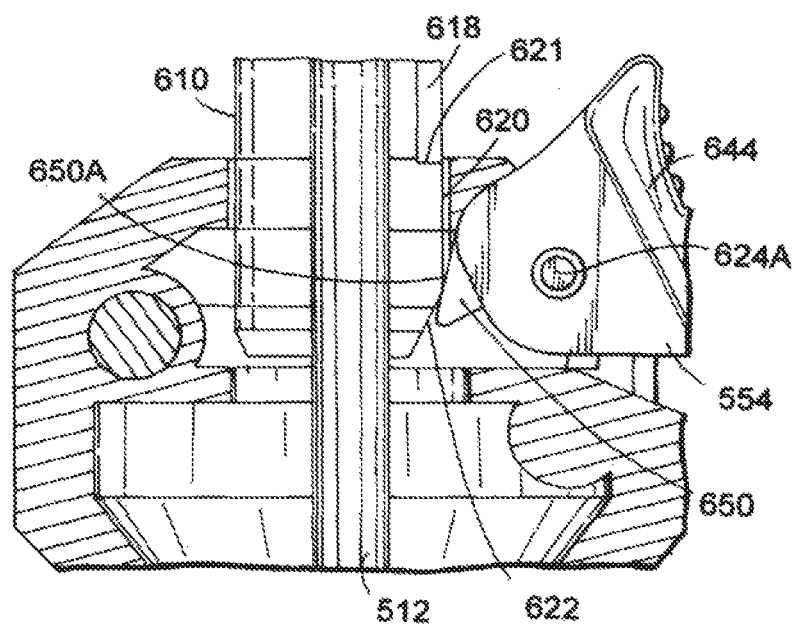
Figure 16C:
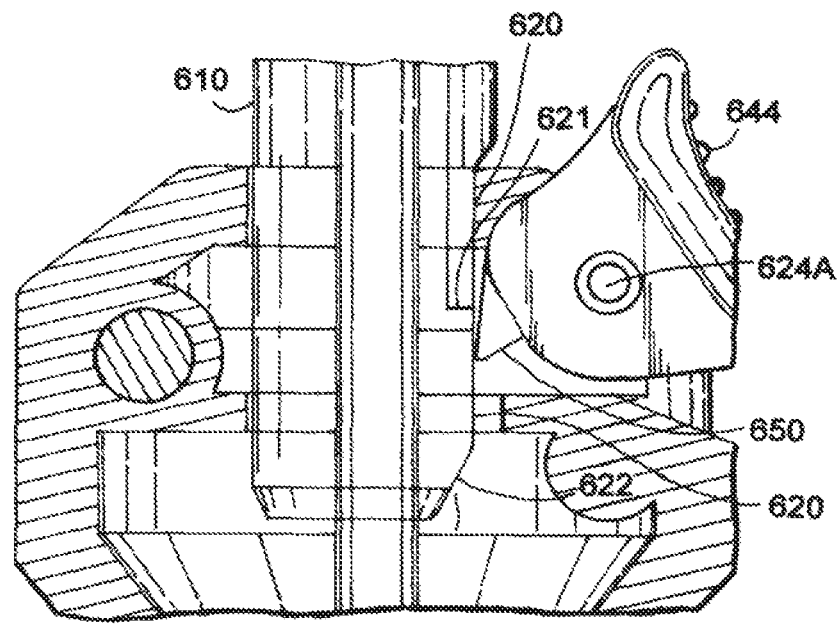
Figure 16E:
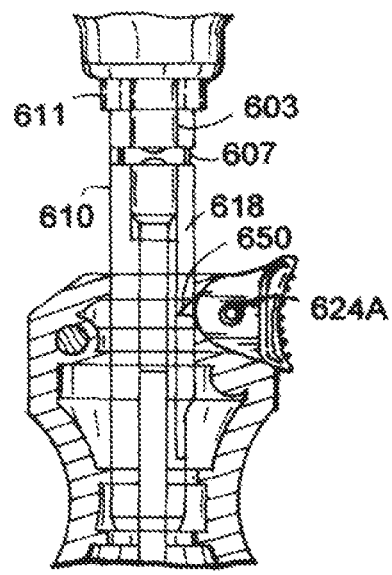
Figure 16D:
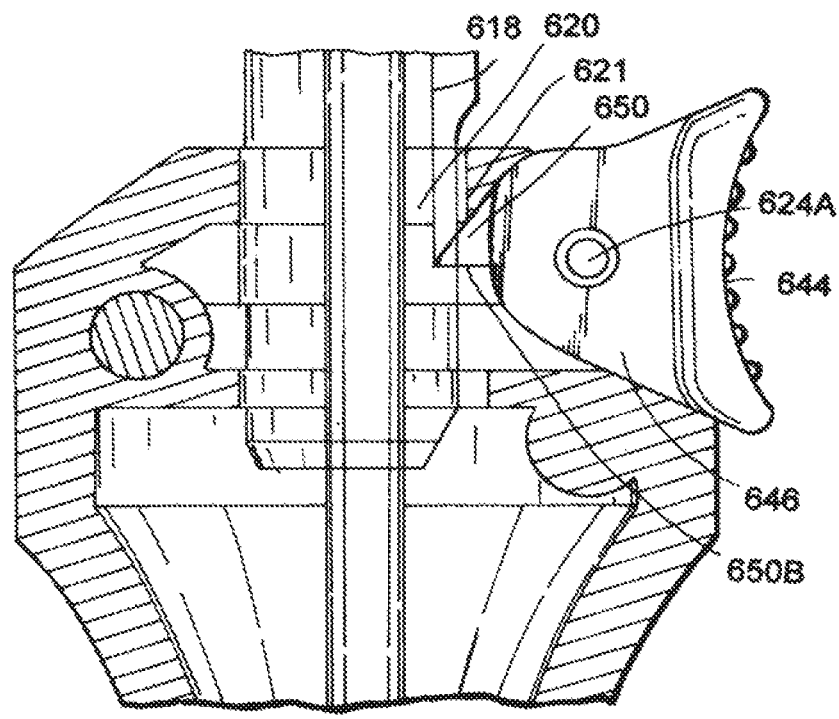

After passing through the skin layers, it is desirable to move the surgical instrument 514 forward so that the end effectors will protect (guard) the bevel of the needle. As seen in FIG. 16B, as the plunger 610 of the surgical instrument 514 is moved forward relative to the needle, the bevel 622 of the plunger works against the angled top surface 650A or the nose 650 of the lever 554 such that the lever 554 rotates counterclockwise against the spring 649 (FIG. 18A). Further movement of the plunger 610 (FIG. 16C) causes the nose 650 to ride in the flattened distal portion 620 of plunger 610 as the end effectors start to emerge from the back of the bevel. When the plunger 610 is moved a little further as seen in FIG. 16D, the nose 650 reaches the groove 618 and the top angled surface 650A of the nose is no longer contacted by the plunger 610. As a result, the spring 649 rotates the lever clockwise until the bottom surface 650B of the nose 650 is generally perpendicular to the axis of the plunger 610 and the nose 650 rides in groove 618. As seen in FIG. 16D, if at this point an attempt is made to retract the surgical instrument from the needle, the flat surface 650B of the nose hits the stop surface 621 of the groove 618 and prevents such movement; i.e., the assembly is in a safety position. When in this safety position, the end effectors extend beyond the very distal tip of the bevel of the needle 512 and guard the tip of the needle as shown in FIG. 17. The only manner of withdrawing the end effectors in order to rearm the needle is to override the stop by manually forcing the lever clockwise, thereby pushing the plunger 610 slightly forward and permitting the nose to ride again in flattened area 620.

Once the assembly has reached the safety position, the operator is free to move the plunger up and down within the operating range of the assembly to cause an opening and closing of the end effectors (as discussed with reference to the previous embodiments of the invention). The operating range is defined by the stop position of FIG. 16D and a position where the top surface of the handle 520 of the needle 512 abuts the head 611 of the plunger 610 of the surgical instrument 514. FIG. 16E shows the assembly in an operating range with the nose 650 of the lever located in the groove 618.

Figure 19B:
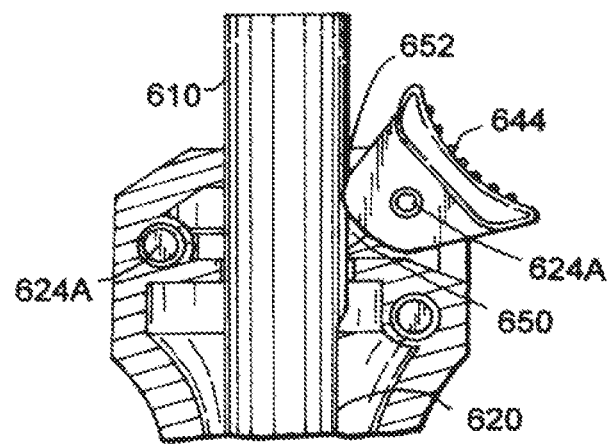
FIGS. 19A-19B are perspective and side views of the proximal portion of the assembly showing the lock mechanism engaging the plunger in a locked position.
Figure 19A:
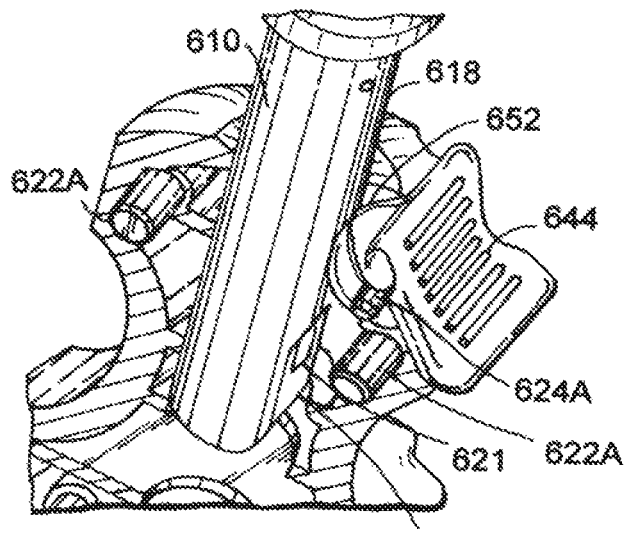

At any point in the operating range of the assembly, the relative location of the instrument 514 and the needle 512 can be fixed or locked. This is accomplished by rotating the lever 554 clockwise against the spring force until the rounded portion 652 of the body 646 of the lever adjacent the top of the nose 650 (which is wider than the nose 650 and the groove 618) frictionally engages the shaft surface 615 of the plunger 614 about the groove 618 as seen in FIGS. 19A and 19B. The frictional forces of this engagement are arranged to be greater than the spring force of spring 649 so that spring 649 does not automatically disengage rounded portion 652 from the surface 615, and preferably large enough to prevent inadvertent movement of the instrument relative to the needle. With this arrangement, large tensile loads applied to the end effectors relative to the needle may result in slippage of the locking mechanism, and large compressive loads can cause unlocking. In normal utilization, if it is desired to unlock the instrument from the needle, the lever 554 may be rotated counterclockwise so that the assembly can be used in its operating range. As with the other embodiments of the invention, removal of assembly 510 from a body can be accomplished with the end effectors opened or closed.

Figure 21B:
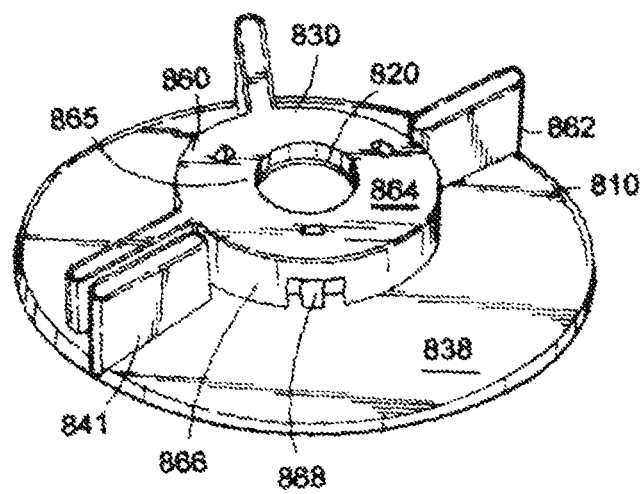
Figure 21G:
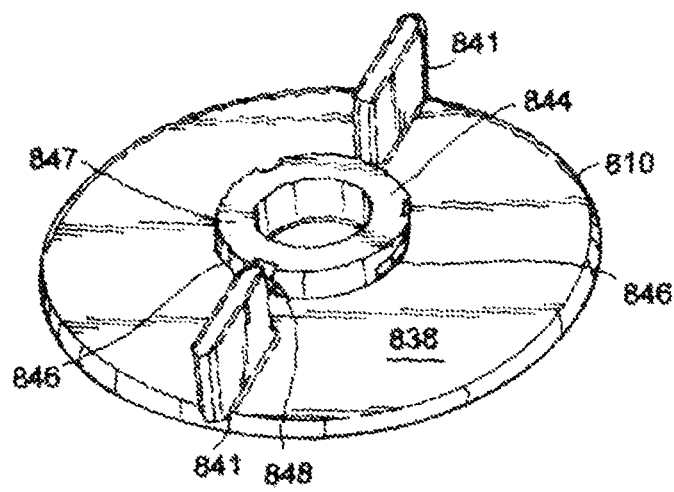
FIG. 21G is a perspective view of the base of FIGS. 21A-21D.

Turning now to FIGS. 21A-21G, a third embodiment of a second fixing means is seen for fixing the surgical assembly relative to the body of the patient. The second fixing means 800 includes three elements: a base 810, a compressible ball 820 and an actuating body 830. The base 810 of the second fixing means 800 seen best in FIGS. 21A, 21D and 21G is essentially a washer, having a flat bottom surface 832 to which an adhesive layer 834 (and a peelable protective paper layer—not shown) may be applied, a frustroconical central opening 836 (see FIG. 21D), and a top surface 838 which defines finger grips 841 and a central ring 844. Ring 844 defines a slightly tapered inner surface 845 (FIG. 21D) for receiving the ball and three separate outer ramps 846 which are recessed into the ring and start at the top surface 847 of the ring and descend as they extend clockwise about the ring until they reach the top washer surface 838. As seen best in FIG. 21G, the ramps 846 are slightly recessed relative the openings on the top surface 847 of the ring to form small ledges 848 for purposes explained hereinafter.

The ball 820 is a preferably hollow plastic ball and is provided with opposite circular openings 851, 852 sized to closely receive the needle shaft of the surgical assembly 510, and a plurality of slits 853 which extend about 120.degree. from the opening 852 in the direction of the axis defined by openings 851, 852. With the slits 853, the ball is compressible such that if a circumferential force is applied to the ball, the lobes 854 formed between the slits 853 will move toward each other. As seen best in FIGS. 21A-21D, the ball 820 is oriented in the ring 844 so that the slits 853 extend downward.

The actuating body 830 is seen best in FIGS. 21A and 21E and is effectively comprises a cap 860 with extending arms 862. The cap 860 has a top wall 864 with a central opening 865 through which the top portion of the ball 820 can extend. The cap 860 also has a side wall 866 with cut-outs which define engagement fingers 868. The engagement fingers 868 have bosses 869 which are sized to ride in the ramps 846 of the ring 844. As seen best in FIG. 21E, the inward facing bosses are ramped or beveled.

In assembly, the ball 820 is placed between the actuating body 830 and the base 810, and the bosses 869 are forced over the ledges 848 and into engagement with the ramps 846. In this position the bottom of the side wall 866 of the cap 860 of the actuating body is spaced relative to the top surface 838 of the washer (see FIG. 21D), and the ball is free to rotate as guided by the ring 844 and central opening 865. Thus, when a shaft of the surgical assembly is inserted through the circular openings 851, 852 of the ball, the shaft will have considerable freedom of movement, limited only by the size of the central opening 865 of the cap 860 and the frustroconical central opening 836 of the base. Preferably, the second fixing means 800 provides the assembly with a freedom of movement of at least forty-five degrees relative to the vertical in all directions. However, when the actuating body 830 is rotated clockwise relative to the base 810 (typically by squeezing arms 862 and 841 together with a thumb and forefinger), the bosses 869 ride down the ramps 846 and pull the body 830 closer to the base 810. Because the ball 820 cannot move downward in the ring, the central opening 865 provides a circumferential force to the ball (i.e., it compresses the ball), thereby forcing the lobes 854 inward, and applying friction to the shaft of the surgical assembly. As a result, not only is the shaft locked in place in the ball 820, but the ball is fixed in its rotational orientation in the fixing means 800. The ball 820 and shaft may be released by rotating the body 830 counterclockwise relative to the base (typically by squeezing the other arms 862, 841 together). The body 830, however, cannot lift of the base 810 because the ledges 848 act as stops.

There have been described and illustrated herein several embodiments of a minimally invasive surgical assembly and methods its use. While particular embodiments of the invention have been described, it is not intended that the invention be limited thereto, as it is intended that the invention be as broad in scope as the art will allow and that the specification be read likewise. Thus, while particular materials for making the needle and surgical instrument have been disclosed, it will be appreciated that other materials may be used as well. In addition, while particular fixing elements and systems have been disclosed for fixing the surgical instrument relative to the needle, it will be understood that other mechanisms can be used. For example, and not by way of limitation, a latch-catch system can be used. Also, while particular fixing elements and systems for fixing the location of the surgical assembly relative to the patient have been described, it will be recognized that other mechanisms can be used for that as well. Furthermore, while particular end effectors such as graspers, lung clamps, etc., have been described for the surgical instrument, it will be understood that instruments with different end effectors such as (but not limited to) dissectors, staplers, scissors, suction/irrigators, clamps, biopsy forceps, etc., can be similarly used. Also, the arms of the end effectors need not be of equal length. Further, while the surgical instrument and needle have been shown as being straight, because of their small diameter they may be bent together by the user, or one or both may be formed with a bend (arc). Moreover, while particular configurations have been disclosed in reference to the handles of the surgical instrument and the needle have been disclosed, it will be appreciated that other configurations could be used as well. In addition, while the needle was described as being a particular size and having a sharp end with a certain angle, it will be appreciated that other size needles can be used and the sharp can be at different angles. It will therefore be appreciated by those skilled in the art that yet other modifications could be made to the provided invention without deviating from its spirit and scope as claimed.

What is claimed is:

1. A surgical assembly, comprising:
   a hollow needle having an outer diameter of 3 mm or smaller and a sharp distal end,
   a first handle coupled to a proximal portion of said hollow needle,
   a surgical instrument having a shaft which extends through said hollow needle and including end effectors at an end of said shaft which are biased open,
   a plunger coupled to a proximal portion of said shaft and coupled to said first handle, said plunger configured for longitudinal movement relative to said first handle, and
   a safety mechanism configured to establish a predetermined working range for said surgical instrument,
   wherein said end effectors have opposed distal tips that are substantially separated from one another in a first extended position and that are disposed in proximate contact to one another in a second extended position,
   wherein the end effectors are moveable relative to the hollow needle to a retracted position wherein the opposed distal tips of the end effectors are positioned proximal relative to the sharp distal end of the hollow needle to thereby expose the sharp distal end, and
   wherein said predetermined working range includes the first extended position and the second extending position, and said safety mechanism includes a stop body biased to limit proximal movement of said surgical instrument relative to said hollow needle beyond said predetermined working range thereby preventing said surgical instrument from being moved from said predetermined working range to said retracted position, said stop body being biased towards a central axis of said plunger to interfere with said plunger to limit proximal movement of said surgical instrument relative to said hollow needle beyond said predetermined working range.

2. The surgical assembly according to claim 1, wherein said hollow needle has an inner surface and said shaft has an outer surface, and said outer surface and said inner surface are sized so that at least a portion of said shaft interferingly slides against said inner surface of said hollow needle, thereby forming a seal which is effective against desufflation.

3. The surgical assembly according to claim 1, further comprising a fixing element coupled to and movable relative to said hollow needle for fixing a relative location of said hollow needle to a patient.

4. The surgical assembly according to claim 3, wherein said fixing element comprises a suction cup extending around said hollow needle.

5. The surgical assembly according to claim 1, wherein said hollow needle is between 13 cm and 18 cm long.

6. The surgical assembly according to claim 1, wherein said end effectors open to a distance between them of more than twice a diameter of said hollow needle.

7. The surgical assembly according to claim 1, wherein said end effectors have first portions coupled to said shaft and extending substantially parallel to a longitudinal axis of said shaft, second portions which angle away from said longitudinal axis at between 6° and 18° in the first extended position, and third portions which angle back from said second portions toward said longitudinal axis.

8. The surgical assembly according to claim 7, wherein said third portions are substantially parallel to said longitudinal axis.

9. The surgical assembly according to claim 1, wherein the hollow needle has a central axis and the sharp distal end of said hollow needle has an end wall angled at substantially 35° relative to the central axis.

10. The surgical assembly according to claim 1, wherein the end effectors are moveable relative to the hollow needle to a partially-extended position wherein the opposed distal tips of the end effectors are positioned outside but close to the sharp distal end of the outer hollow needle such that the end effectors act as an obturator for protecting against accidental trauma caused by the sharp distal end of the outer hollow needle.

11. The surgical assembly according to claim 1, wherein a longitudinal groove is formed on said plunger, said longitudinal groove having a stop surface at a distal portion of said plunger, and
wherein said longitudinal groove receives a member of said stop body and said stop surface engages said member of said stop body to limit proximal movement of said surgical instrument relative to said hollow needle beyond said predetermined working range.

12. The surgical assembly according to claim 11, further comprising a second handle coupled to a proximal portion of said plunger via a rotational linkage.

13. The surgical assembly according to claim 12, wherein said plunger has a tubular opening formed in a proximal end of said plunger, and said tubular opening receives a post of said second handle.

14. The surgical assembly according to claim 13, wherein the post has an annular groove formed therein, and said groove receives a pin through a pin hole formed in said plunger to couple said second handle to said plunger while permitting relative rotation therebetween.

15. The surgical assembly according to claim 1,
wherein a member of said stop body includes a nose, and said stop body is rotatably coupled to said first handle,
wherein said plunger includes a groove, and
wherein the nose of said stop body and the groove of said plunger interact with each other to limit proximal movement of said surgical instrument relative to said hollow needle to prevent said surgical instrument from being moved from said predetermined working range back to said retracted position.

16. The surgical assembly according to claim 15,
wherein the groove of said plunger has a flattened distal portion forming a stop surface,
wherein the nose has a bottom surface, and said stop body is biased such that the bottom surface extends generally perpendicular to an axis of said plunger, and
wherein the stop surface interacts with the bottom surface of said stop body to limit proximal movement of said surgical instrument relative to said hollow needle.

17. The surgical assembly according to claim 1,
wherein said first handle has an outer surface including a lower ribbed portion and an upper ribbed portion, and
wherein said first handle includes a hourglass shaped waist between the lower ribbed portion and the upper ribbed portion.

18. The surgical assembly according to claim 17, wherein the upper ribbed portion includes an opening for housing said safety mechanism.

* * * * *

UNITED STATES PATENT AND TRADEMARK OFFICE
CERTIFICATE OF CORRECTION

PATENT NO. : 10,166,038 B2  
APPLICATION NO. : 15/345716  
DATED : January 1, 2019  
INVENTOR(S) : Sundaram Ravikumar et al.

It is certified that error appears in the above-identified patent and that said Letters Patent is hereby corrected as shown below:

In the Claims

In Claim 10, Column 17, Line 22, "of the outer hollow needle" should be -- of the hollow needle --;
In Claim 10, Column 17, Line 24, "of the outer hollow needle" should be -- of the hollow needle --.

Signed and Sealed this
Fifth Day of March, 2019

Andrei Iancu
*Director of the United States Patent and Trademark Office*